(12) United States Patent
Falardeau et al.

(10) Patent No.: US 7,358,241 B2
(45) Date of Patent: *Apr. 15, 2008

(54) COMPOSITIONS AND METHODS COMPRISING FARNESYL DIBENZODIAZEPINONES FOR TREATING NEOPLASTIC CELLS AND CONDITIONS

(75) Inventors: Pierre Falardeau, Westmount (CA); Francois Berger, Meylan (FR); Henriette Gourdeau, Montreal (CA); James B. McAlpine, Montreal (CA); Chris M. Farnet, Montreal (CA); Violetta Dimitriadou, Saint-Anne-de Bellevue (CA)

(73) Assignee: Thallion Pharmaceuticals, Inc., Montreal (CA)

( * ) Notice: Subject to any disclaimer, the term of this patent is extended or adjusted under 35 U.S.C. 154(b) by 42 days.

This patent is subject to a terminal disclaimer.

(21) Appl. No.: 11/130,295

(22) Filed: May 16, 2005

(65) Prior Publication Data

US 2006/0079508 A1 Apr. 13, 2006

Related U.S. Application Data

(63) Continuation-in-part of application No. 10/951,436, filed on Sep. 27, 2004, now Pat. No. 7,186,713, which is a continuation-in-part of application No. 10/762,107, filed on Jan. 21, 2004, now Pat. No. 7,101,872.

(60) Provisional application No. 60/518,286, filed on Nov. 10, 2003, provisional application No. 60/492,997, filed on Aug. 7, 2003, provisional application No. 60/441,126, filed on Jan. 21, 2003.

(51) Int. Cl.
*A61P 35/00* (2006.01)
*A61P 35/02* (2006.01)
(52) U.S. Cl. .................................. 514/220
(58) Field of Classification Search ............... 514/220
See application file for complete search history.

(56) References Cited

U.S. PATENT DOCUMENTS

| | | | |
|---|---|---|---|
| 3,854,480 A | 12/1974 | Zaffaroni | |
| 4,452,775 A | 6/1984 | Kent | |
| 5,039,660 A | 8/1991 | Leonard | |
| 5,541,181 A | 7/1996 | Ohkuma et al. | 514/220 |
| 2003/0109518 A1 | 6/2003 | Lu et al. | 514/221 |
| 2003/0219718 A1 | 11/2003 | Weber et al. | 435/4 |
| 2004/0220179 A1 | 11/2004 | Lu et al. | 514/217.03 |

FOREIGN PATENT DOCUMENTS

CA 2248820 9/1997

OTHER PUBLICATIONS

Igarashi, et al., "Revision of the Structure Assigned to the Antibiotic BU-4664L from *Micromonopora*", Journal of Antibiotics (2005), V. 58, No. 7, pp. 350-352.

Correction to p. 352. Igarashi, et al., "Revision of the Structure Assigned to the Antibiotic BU-4664L from *Micromonopora*", Journal of Antibiotics (2005), V. 58, No. 7, pp. 350-352.

Charan, et al., "A New Antimicrobial Alkaloid from a *Micromonospora* sp.", Abstract and Figures from Poster Presentation #p:157 at the 44th Annual Meeting of the American Society of Pharmacognosy, Chapel Hill, N.C., Jul. 12-16, 2003.

Embley and Stackebrandt, "The molecular phylogeny and systematics of the actinomycetes", Annual Review Microbiology (1994), V. 48, pp. 257-289.

British Journal of Cancer (1998) vol. 77(1) pp. 1-11 United Kingdom Co-ordinating Committee on Cancer Reseach (UKCCCR) Guidelines for the Welfare of Animals in Experimental Neoplasia (Second Edition).

Charan et al., "Diazepinomicin, a new antimicrobial alkaloid from a marine *Micromonospora* sp", Journal of Nat Prod. Aug. 2004, 67(8), pp. 1431-1433.

Alberts, et al., Molecular Biology of the Cell (3rd edition), Garland Publishing, Inc (1994) pp. 1255-1294.

Alberts B. et al., Molecular Biology of the Cell (3d ed. 1994) pp. 1255-1294.

Berge S. et al., Journal of Pharmaceutical Sciences (1977) vol. 66, No. 1, pp. 1-19 "Pharmaceuticals Salts".

Rooseboom M. et al., Pharmacol. Reviews (2004), vol. 56, pp. 53-102 "Enzyme-Catalyzed Activiation of Anticancer Prodrugs".

Goodfellow M., Bergey's Manual of Systematic Bacteriology (1989) vol. 4, pp. 2333-2339 "Suprageneric Classification of Actinomycetes".

Embley and Stackebrandt, Annu. Rev. Microbiol. (1994) vol. 48, pp. 257-289 "The molecular phylogeny and systematics of the actinomycetes".

Carayon P. et al., Blood (1996 vol. 87, No. 8, pp. 3170-3178 "Involvement of Peripheral Benzodiazepine Receptors in the Protection of Hematopoietic Cells Against Oxygen Radical Damage".

(Continued)

*Primary Examiner*—Bruck Kifle

(57) ABSTRACT

This invention relates to methods of inhibiting growth and/or proliferation of a neoplastic cell, and methods of treating neoplasms using the farnesylated dibenzodiazepinone compound of Formula I. The invention includes pharmaceutical compositions comprising the compound of Formula I:

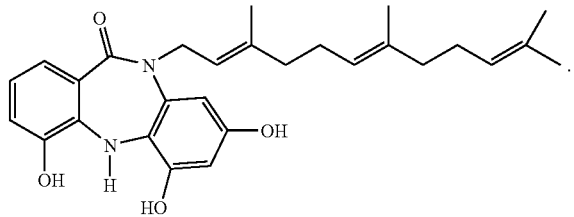

21 Claims, 11 Drawing Sheets

OTHER PUBLICATIONS

Hirsch T. et al., Experimental Cell Research (1998) vol. 241, No. 2, pp. 426-434 "PK11195, a ligand of the mitochondrial benzodiazepine receptor, facilitates the induction of apoptosis and reverses Bcl-2-mediated cytoprotection".

Bono F. et al., Biochem. Biophys. Res. Comm. (1999) vol. 265, No. 2, pp. 457-461 "Peripheral benzodiazepine receptor agonists exhibit potent antiapoptotic activities".

Miettinen H. et al., Cancer Res. (1995) vol. 55, No. 12, pp. 2691-2695 "Expression of peripheral-type benzodiazepine receptor and diazepam binding inhibitor in human astrocytomas: relationship to cell proliferation".

Katz Y. et al., Clin Sci. (1990) vol. 78, No. 2, pp. 155-158 "Increased density of peripheral benzodiazepine-binding sites in ovarian carcinomas as compared with benign ovarian tumours and normal ovaries".

Katz Y. et al., Oncology (1990) vol. 47, No. 2, pp. 139-142 "Increase in peripheral benzodiazepine binding sites in colonic adenocarcinoma".

Venturini I. et al., Life Sci. (1999) vol. 65, No. 21, pp. 2223-2231 "Increased expression of peripheral benzodiazepine receptors and diazepam binding inhibitor in human tumors sited in the liver".

Verma A. et al., Mol. Med. (1998) vol. 4, No. 1, pp. 40-45 "Photodynamic tumor therapy: mitochondrial benzodiazepine receptors as a therapeutic target".

Kupczyk-Subotkowska L. et al., J. Med. Chem. (1997) vol. 40, No. 11, pp. 1726-1730 "Modulation of melphalan resistance in glioma cells with a peripheral benzodiazepine receptor ligand-melphalan conjugate".

Guo P. et al., Cancer Chemother. Pharmacol. (2001) vol. 48, No. 2, pp. 169-176 "Targeted delivery of a peripheral benzodiazepine receptor ligand-gemcitabine conjugate to brain tumors in a xenograft model".

Wang J. et al., Prod. Natl. Acad. Sci. USA (1984) vol. 81, pp. 753-756 "Benzodiazepines that bind at peripheral sites inhibit cell proliferation".

Landau M. et al., J. Biochem. Pharmacol. (1998) vol. 56, No. 8, pp. 1029-1034 "Antiproliferative and differentiating effects of benzodiazepine receptor ligands on B16 meanoma cells".

Stoebner PE et al., Cell Death Differ. (2001) vol. 8, No. 7, pp. 747-753 "Transient protection by peripheral benzodiazepine receptors during the early events of ultraviolet light-induced apoptosis".

Jakubikova J. et al., Neoplasma (2002) vol. 49, No. 4, pp. 231-236 "PK11195, an isoquinoline carboxamide ligand of the mitochondrial benzodiazepine receptor, increased drug uptake and facilitated drug-induced apoptosis in human multidrug-resistant leukemia cells in vitro".

Decaudin D. et al., Cancer Res. (2002) vol. 62, No. 5, pp. 1388-1393 "Peripheral Benzodiazepine Receptor Ligands Reverse Apoptosis Resistance of Cancer Cells in Vitro and in Vivo".

Childs S., Imp. Adv. Oncol. (1994) pp. 21-36 "The MDR superfamily of genes and its biological implications".

Fan D. et al., Reversal of Multidrug Resistance in Cancer, ed. Kellen, J.A. (1993) pp. 93-125.

Cole S.P.C. et al., Science (1992) vol. 258, pp. 1650-1654 "Overexpression of a transporter gene in a multidrug-resistant human lung cancer cell line".

Scheffer G.L. et al., Nat. Med. (1995) vol. 1, No. 6, pp. 578-582 "The drug resistance-related protein LRP is the human major vault protein".

Beck W.T., J. Natl., Cancer Inst. (1989) vol. 81, No. 22, pp. 1683-1685 "Unknotting the complexities of multidrug resistance: the involvement of DNA topoisomerases in drug action and resistance".

Freireich EJ. et al., Cancer Chemother. Reports (1966) vol. 50, No. 4, pp. 219-244 "Quantitative comparison of toxicity of anticancer agents in mouse, rat, hamster, dog, monkey, and man".

Workman et al., British Journal of Cancer (1998) vol. 77, pp. 1-10 United Kingdom Co-ordinating Committee on Cancer Research (UKCCCR) Guidelines for the Welfare of Animals in Experimental Neoplasia (Second Edition).

Premont J. et al., Biochim Biophys Acta. (1975) vol. 381, No. 2, pp. 368-376 "[3H] norepinephrine binding by rat glial cells in culture. Lack of correlation between binding and adenylate cyclase activation".

Le Fur G. et al., Life Sci. USA (1983) vol. 33, No. 5, pp. 449-457 "Differentiation between two ligands for peripheral benzodiazepine binding sites, [3H]RO5-4864 and [3H]PK 11195, by thermodynamic studies".

Damm HW et al., Res. Comm. Chem. Pathol. Pharmacol. (1978) vol. 22, pp. 597-600' [3H] Flunitrazepam: its advantages as a ligand for the identification of benzodiazepine receptors in rat brain membranes.

Speth RC. et al., Life Sci. (1979) vol. 24, No. 4, pp. 351-357 "Benzodiazepine receptors: temperature dependence of [H3] flunitrazepam binding".

De George JJ. et als., Cancer Chemother. Pharmacol. (1998) vol. 41, pp. 173-185 "Regulatory considerations for preclinical development of anticancer drugs".

Lash L, Toxicological Sciences (2003) vol. 74, pp. 1-3 "The mitochondrial benzodiazepine receptor as a potential target protein for drug development: Demonstration of functional significance with cell lines exhibiting differntial expression of Bcl-2".

Pawlikowski M. et al., Acta Neurol. Scand. (1988) pp. 231-233 "Inhibition of cell proliferation of human gliomas by benzodiazepines in vitro".

Decaudin D. et al., Cancer Research (2002) vol. 62, pp. 1388-1393 "Peripheral Benzodiazepine Receptor Ligands Reverse Apoptosis Resistance of Cancer Cells in vitro and in vivo".

Broaddus W. et al., Brain Research (1990) vol. 518, pp. 199-208 "Peripheral-type benzodiazepine receptors in human glioblastomas: pharmacologic characterization and photoaffinity labeling of ligand recognition site".

Chelli B. et al., Biochemical Pharmacology (2004) vol. 68, pp. 125-134 "Peripheral benzodiazepine receptor ligands: mitochondrial transmembrane potential depolarization and apoptosis induction in rat C6 glioma cells".

Anderson and Lokich, "Cancer Chemotherapy and Infusional Scheduling," Oncology (1994) vol. 8, No. 5, pp. 99-111.

Craig, et al., Modern Pharmacology, 4th edition (1994) Little, Brown and Company, pp. 669-670.

Greidanus, et al., "Continuous infusion of low-dose doxorubicin, epirubicin and mitoxantrone in cancer chemotherapy: a review," Pharm. Weekbl. Sci. (1998), vol. 10, No. 6, pp. 237-245.

Wils, J.A., "High-Dose Infusional 5-FU in the Treatment of Advanced Colorectal Cancer: A Summary of the European Experience," J. Infus. Chemotherapy (1996), vol. 6, No. 3, pp. 145-148.

Healing, et al., Handbook of Pre-clinical Continuous Intravenous Infusion (2000) Taylor & Francis.

FIGURE 4
Saline
ECO-04601
(20 mg/kg)

Antitumor efficacy of ECO-4601 against orthotopic C6 glioma tumor xenograft

Antitumor Efficacy of ECO-4601 Against Human Breast Tumor (MDA-MB-231) Xenografts in Female Harlan Nude Mice

COMPOSITIONS AND METHODS COMPRISING FARNESYL DIBENZODIAZEPINONES FOR TREATING NEOPLASTIC CELLS AND CONDITIONS

CROSS-REFERENCING TO RELATED APPLICATION

This application is a CIP of U.S. application Ser. No. 10/951,436, filed Sep. 27, 2004, now U.S. Pat. No. 7,186,713 which is a CIP of U.S. application Ser. No. 10/762,107, filed Jan. 21, 2004, now U.S. Pat. No. 7,101,872 which claims priority to U.S. Provisional Application 60/441,126, filed Jan. 21, 2003; U.S. Provisional Application 60/492,997, filed Aug. 7, 2003; and U.S. Provisional Application 60/518,286, filed Nov. 10, 2003. The entire teachings of the above applications are incorporated herein by reference.

FIELD OF INVENTION

This invention relates to compositions and methods for inhibiting growth and proliferation of a neoplastic cell, and methods of treating neoplasms in a mammal using the compound of Formula I or a pharmaceutically acceptable salt or prodrug thereof.

BACKGROUND

Neoplasia occurs when normal body cells are changed, proliferating without regard to normal cellular restraints, and invade and colonize areas of the body normally occupied by other cells. See B. Alberts et al., *Molecular Biology of the Cell* 1255-1294 (3d ed. 1994). According to the American Cancer Society, one-half of American men and one-third of American women will at some point in their lives develop a neoplastic disorder.

Abnormal cell proliferation is usually characterized by an increase rate of division and in some cases uncontrolled growth. One example of a proliferative cell disorder is a tumor or neoplasm. In addition to posing a serious risk in and of themselves, primary malignant neoplasms are particularly problematic given their tendency to invade surrounding tissues and metastasize to distant organs in the body. To date, the most frequently used methods for treating neoplasia include surgical procedures, radiation therapy, and drug therapies, and combinations of the foregoing. These methods involve significant risk (e.g., of infection, death) to the patient. More importantly, the probability of eliminating all malignant cells is small, particularly if the zone of the malignant growth is not well defined or if the primary tumor has metastasized by the time of surgery. Achieving therapeutic doses effective for treating neoplasm is often limited by the toxic side effects of the anti-cancer agent on normal, healthy tissue. An ideal anti-cancer agent has tissue specificity, thereby reducing side-effects on normal (dividing) cells. There is a need in the art for novel cancer therapeutics which have higher efficacy, specificity, or reduced side effects.

SUMMARY OF THE INVENTION

The invention provides a method for inhibiting the growth or proliferation of a neoplastic cell, the method comprising contacting the neoplastic cell with a farnesyl dibenzodiazepinone such that growth or proliferation of the neoplastic cell is inhibited.

In another aspect, the invention provides a method of treating neoplasm in a mammal, comprising the step of administering to the mammal a therapeutically effective amount of the compound of Formula I, or a pharmaceutically-acceptable salt or prodrug of the compound of Formula I:

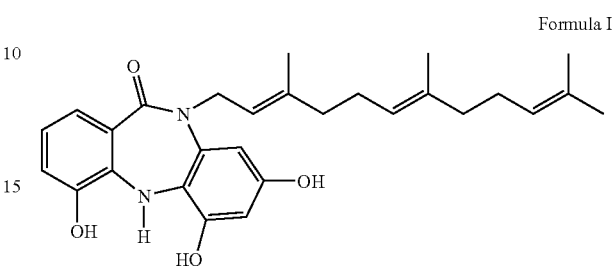

Formula I such that the neoplasm is treated.

In another aspect, the invention provides a method of inducing apoptosis of a neoplasm in a mammal, comprising the step of administering to the mammal a therapeutically effective amount of the compound of Formula I, or a pharmaceutically acceptable salt or prodrug, such that the neoplasm is treated or controlled.

In another aspect, the invention a compound of Formula I, or a pharmaceutically acceptable salt or prodrug thereof, for the inhibition of the growth or proliferation of a neoplastic cell in a mammal. In another embodiment, the invention provides a compound of Formula I, or a pharmaceutically acceptable salt or prodrug thereof, for inducing apoptosis in a neoplastic cell. In a further aspect, the invention provides a compound of Formula I, or a pharmaceutically acceptable salt or prodrug thereof, for the treatment of neoplasia in a mammal. In another aspect, the invention provides a pharmaceutical composition comprising the compound of Formula I, or a pharmaceutically acceptable salt or prodrug thereof, for the treatment of neoplasia in a mammal. In one embodiment, the pharmaceutical composition for treating neoplasia comprises the compound of Formula I and at least one further therapeutic agent selected from the group consisting of chemotherapeutic agents, biological response modifiers, multidrug reversing agents and target specific antitumor agents.

In one embodiment, the cancer cell, neoplasm or pre-cancerous or cancerous condition, in the above-mentioned methods and compositions, is selected from leukemia, melanoma, breast cancer, lung cancer, pancreatic cancer, ovarian cancer, renal cancer, colon or colorectal cancer, prostate cancer, and CNS cancer. In another embodiment, the cancer cell, and pre-cancerous or cancerous condition, in the above-mentioned methods and uses, is selected from leukemia, breast cancer, prostate cancer, and CNS cancer.

BRIEF DESCRIPTION OF THE DRAWINGS

FIG. 4 shows micrographs of tumor sections from mice bearing glioblastoma tumors and treated with saline or the compound of Formula I. The cell density of tumor treated with the compound of Formula I appears decreased and nuclei from tumor cells treated with the compound of Formula I are larger and pycnotic suggesting a cytotoxic effect.

Figure 1:
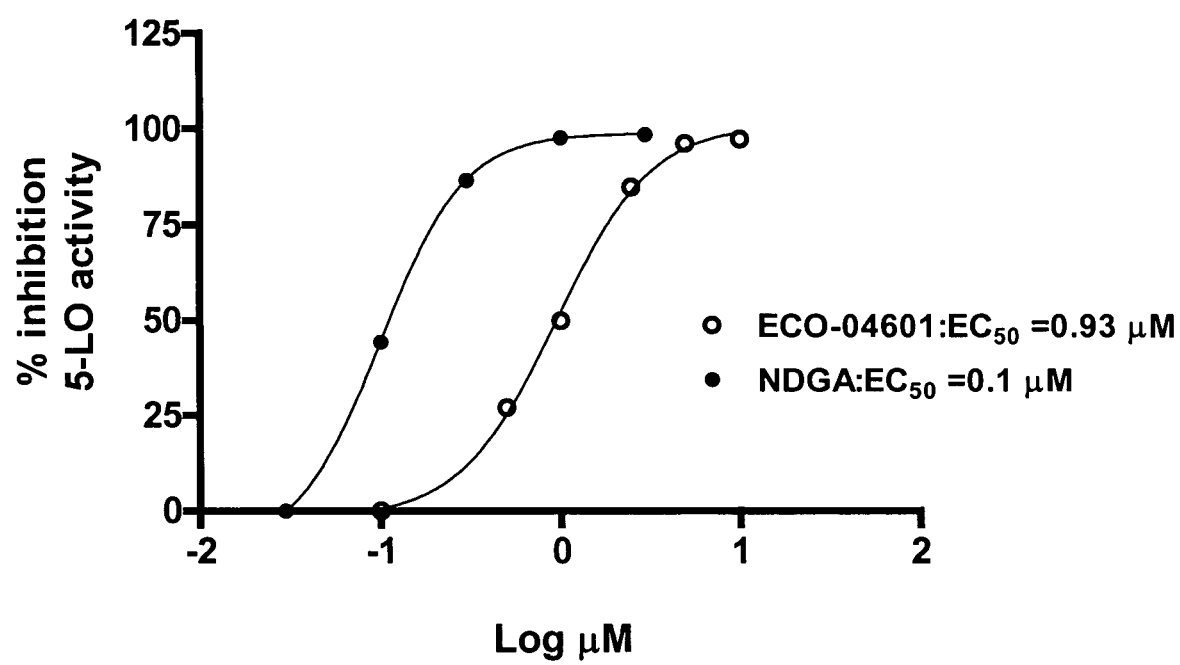
FIG. 1 shows the in vitro anti-inflammatory activity of the compound of Formula I. Graph shows percent inhibition of 5-lipoxygenase activity plotted against the Log μM concentration of the compound of Formula I and NDGA; the $EC_{50}$ of the compound of Formula I is 0.93 μM.

DETAILED DESCRIPTION OF THE INVENTION:

The present invention provides methods for inhibiting proliferation and growth of a neoplastic cell. The methods comprise treating the cell with a farnesyl dibenzodiazepinone compound, such as the compound of Formula I, referred to herein as "ECO-4601." The present invention also provides methods for treating a neoplastic disorder in a mammal. The methods comprise administering a pharmaceutically effect amount of ECO-4601, or pharmaceutically-acceptable salt or prodrug thereof to a mammal in need of treatment.

The invention further provides pharmaceutically acceptable salts and prodrugs of the compound of Formula I and methods for obtaining such compounds. One method of obtaining the compound is by cultivating *Micromonospora* sp. strains 046-ECO11, or [S01]046 or a mutant or a variant thereof, under suitable *Micromonospora* culture conditions, such as the fermentation protocol described hereinbelow.

The present invention also provides pharmaceutical compositions comprising the compound of Formula I and its pharmaceutically acceptable salts and prodrugs.

I. Farnesylated Dibenzodiazepinone Compounds

In one aspect, the invention relates to a novel farnesyl dibenzodiazepinone having the chemical structure represented by Formula I below:

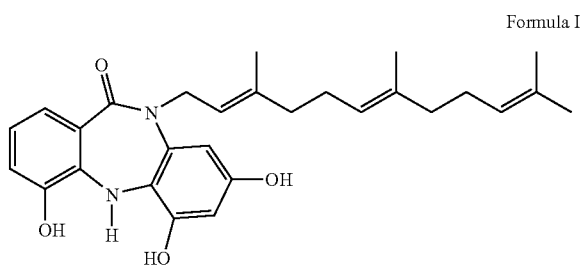

Formula I

The compound of Formula I may be described as a dibenzodiazepinone having a farnesyl substituent located on the nitrogen atom in the 10 position of the dibenzodiazepine ring (i.e., the amide nitrogen in the diazepinone ring), and three phenolic hydroxy substituents in the 4,6 and 8 positions of the dibenzodiazepinone ring. The compound of Formula I may be characterized by any one or more of its physicochemical and spectral properties given below, such as its mass, UV, and NMR spectroscopic data. Mass was determined by electrospray mass spectrometry to be 462.6 g/mol; UV=221 nm with a shoulder at 290 nm. NMR data were collected using MeOH-d4, including proton, carbon, and multidimensional pulse sequences gDQCOSY, gHSQC, gHMBC, and NOESY.

As used herein, the term "farnesyl dibenzodiazepinone" refers to the compound of Formula I, namely 10-farnesyl-4,6,8-trihydroxy-dibenzodiazepin-11-one, sometimes designated herein as "ECO-4601." The term "farnesyl dibenzodiazepinone" also includes pharmaceutically-acceptable salts and prodrugs of ECO-4601.

The term "pharmaceutically acceptable salt" refers to both acid addition salts and base addition salts. The nature of the salt is not critical, provided that it is pharmaceutically acceptable. Exemplary acid addition salts include, without limitation, hydrochloric, hydrobromic, hydroiodic, nitric, carbonic, sulphuric, phosphoric, formic, acetic, citric, tartaric, succinic, oxalic, malic, glutamic, propionic, glycolic, gluconic, maleic, embonic (pamoic), methanesulfonic, ethanesulfonic, 2-hydroxyethanesulfonic, pantothenic, benzenesulfonic, toluenesulfonic, sulfanilic, mesylic, cyclohexylaminosulfonic, stearic, algenic, β-hydroxybutyric, malonic, galactaric, galacturonic acid, glucoronic acid and the like. Suitable pharmaceutically acceptable base addition salts include, without limitation, metallic salts made from aluminium, calcium, lithium, magnesium, potassium, sodium and zinc or organic salts made from N,N'-dibenzylethylenediamine, chloroprocaine, choline, diethanolamine, ethylenediamine, N-methylglucamine, lysine, procaine and the like. Additional examples of pharmaceutically acceptable salts are listed in Berge et al., *Journal of Pharmaceutical Sciences* (1977) vol 66, no 1, 1-19. All of these salts may be prepared by conventional means from a farnesyl dibenzodiazepinone by treating the compound with the appropriate acid or base.

The term "pharmaceutically acceptable prodrug" means any pharmaceutically acceptable ester, salt of an ester or any other derivative of a farnesyl dibenzodiazepinone, which upon administration to a mammal is capable of providing, either directly or indirectly, a compound of Formula I or a biologically active metabolite or residue thereof. Particularly favored salts or prodrugs are those with improved properties, such as solubility, efficacy, or bioavailability of the compounds of this invention when such compounds are administered to the mammal (e.g., by allowing an orally administered compound to be more readily absorbed into the blood) or which enhance delivery of the parent compound to a biological compartment (e.g., the brain or lymphatic system) relative to the parent species. Exemplary prodrugs of the compound of Formula I include compounds wherein one or more of the 4, 6 and 8-hydroxy groups is bounded to any group that, when administered to a mammalian subject, is cleaved to form the free hydroxyl group. Examples of prodrugs include, but are not limited to, acetate, formate, hemisuccinate, benzoate, dimethylaminoacetate and phosphoryloxycarbonyl derivatives of hydroxy functional groups; dimethylglycine esters, aminoalkylbenzyl esters, aminoalkyl esters or carboxyalkyl esters of hydroxy functional groups. Carbamate and carbonate derivatives of the hydroxy groups are also included. Derivatizations of hydroxyl groups also encompassed, are (acyloxy)methyl and (acyloxy)ethyl ethers, wherein the acyl group is an alkyl group optionally substituted with groups including, but not limited to, ether, amino and carboxylic acid functionalities, or where the acyl group is an amino acid ester. Also included are phosphate and phosphonate esters, sulfate esters, sulfonate esters, which are in alkylated (such as bis-pivaloyloxymethyl (POM) phosphate triester) or in the salt form (such as sodium phosphate ester ($-P(O)O^-_2Na^+_2$)). For further examples of prodrugs used in anticancer therapy and their metabolism, see Rooseboom et al (2004), *Pharmacol. Rev.*, vol 56, 53-102. When the prodrug contains an acidic or basic moiety, the prodrug may also be prepared as its pharmaceutically acceptable salt.

II. Method of Making a Farnesyl Dibenzodiazepinone by Fermentation

The compound of Formula I may be obtained by cultivating a novel strain of *Micromonospora*, namely *Micromonospora* sp. strain 046-ECO11 or strain [S01]046. Strain 046-ECO11 and strain [S01]046 were deposited on Mar. 7, 2003, and Dec. 23, 2003, respectively, with the International Depository Authority of Canada (IDAC), Bureau of Microbiology, Health Canada, 1015 Arlington Street, Winnipeg, Manitoba, Canada R3E 3R2, and were assigned Accession Nos. IDAC 070303-01 and IDAC 231203-01, respectively. The deposit of strains was made under the terms of the Budapest Treaty on the International Recognition of the Deposit of Microorganisms for Purposes of Patent Procedure. The deposited strains will be irrevocably and without restriction or condition released to the public upon the issuance of a patent. The deposited strains are provided merely as convenience to those skilled in the art and are not an admission that a deposit is required for enablement, such as that required under 35 U.S.C. §112.

It is to be understood that the present invention is not limited to use of the particular strains 046-ECO11and [S01] 046. Rather, the present invention contemplates the use of other farnesyl dibenzodiazepinone-producing organisms, such as mutants or variants of 046-ECO11 and [S01]1046 that can be derived from these organisms by known means such as X-ray irradiation, ultraviolet irradiation, treatment with nitrogen mustard, phage exposure, antibiotic resistance selection and the like; or through the use of recombinant genetic engineering techniques, as described in Section IV of copending U.S. Ser. No. 10/951,436.

The farnesyl dibenzodiazepinone of the present invention may be biosynthesized by various microorganisms. Microorganisms that may synthesize the compounds of the present invention include but are not limited to bacteria of the order Actinomycetales, also referred to as *actinomycetes*. Non-limiting examples of members belonging to the genera of *Actinomycetes* include *Nocardia, Geodermatophilus, Actinoplanes, Micromonospora, Nocardioides, Saccharothrix, Amycolatopsis, Kutzneria, Saccharomonospora, Saccharopolyspora, Kitasatospora, Streptomyces, Microbispora, Streptosporangium*, and *Actinomadura*. The taxonomy of *actinomycetes* is complex and reference is made to Goodfellow, *Suprageneric Classification of Actinomycetes* (1989); *Bergey's Manual of Systematic Bacteriology*, Vol. 4 (Williams and Wilkins, Baltimore, pp. 2322-2339); and to Embley and Stackebrandt, "The molecular phylogeny and systematics of the *actinomycetes*," *Annu. Rev. Microbiol.* (1994) 48:257-289, each of which is hereby incorporated by reference in its entirety, for genera that may synthesize the compounds of the invention.

A microorganism producing the farnesylated dibenzodiazepinone is cultivated in culture medium containing known nutritional sources for actinomycetes. Such media having assimilable sources of carbon, nitrogen, plus optional inorganic salts and other known growth factors at a pH of about 6 to about 9. Suitable media are well known in the art as described, for example, in WO 2004/065591 (published US patent application US 2005/0043297). The microorganism is cultivated at incubation temperatures of about 18° C. to about 40° C. for about 3 to about 40 days. The culture media inoculated with the microorganism is aerated by incubating the inoculated culture media with agitation, for example, shaking on a rotary shaker, a shaking water bath, or in a fermentator. Aeration may also be achieved by the injection of air, oxygen or an appropriate gaseous mixture to the inoculated culture media during incubation. Following cultivation, the farnesyl dibenzodiazepinone is extracted and isolated from the cultivated culture media by techniques known to a skilled person in the art, including, centrifugation, chromatography, adsorption, filtration. For example, the cultivated culture media is mixed with a suitable organic solvent such as n-butanol, n-butyl acetate or 4-methyl-2-pentanone, and the organic layer is separated by centrifugation. The solvent is removed by evaporation to dryness or by evaporation to dryness under vacuum. The resulting residue may be optionally reconstituted with water, ethanol, ethyl acetate, methanol or a mixture thereof, and re-extracted in a two-phase system. Extraction with a suitable organic solvent such as hexane, acetonitrile, ethyl acetate, methanol and carbon tetrachloride, methylene chloride or a mixture thereof may be used to remove impurities. Following removal of the solvent, the farnesyl dibendizepinone may be further purified by the use of standard techniques, such as chromatography.

III. Pharmaceutical Compositions Comprising Farnesyl Dibenzodiazepinones

The farnesyl dibenzodiazepinone may be formulated into a pharmaceutical composition comprising a compound of Formula I in combination with a pharmaceutical acceptable carrier. The pharmaceutical composition comprising the farnesyl dibenzodiazepinone is useful for treating diseases and disorders associated with uncontrolled cellular growth and proliferation, such as a neoplastic condition. The pharmaceutical composition comprising the farnesyl dipenzidiazepinone may be packaged into a convenient commercial package providing the necessary materials, such as the pharmaceutical composition and written instructions for its use in treating a neoplastic condition, in a suitable container.

The compounds of the present invention, or pharmaceutically acceptable salts thereof, can be formulated for oral, sublingual, intranasal, intraocular, rectal, transdermal, mucosal, topical or parenteral administration for the therapeutic or prophylactic treatment of neoplastic and proliferative diseases and disorders. Parenteral modes of administration include without limitation, intradermal, subcutaneous (s.c., s.q., sub-Q, Hypo), intramuscular (i.m.), intravenous (i.v.), intraperitoneal (i.p.), intra-arterial, intramedulary, intracardiac, intra-articular (joint), intrasynovial (joint fluid area), intracerebral or intracranial, intraspinal, intracisternal, and intrathecal (spinal fluids). Any known device useful for parenteral injection or infusion of drug formulations can be used to effect such administration. For oral and/or parental administration, compounds of the present invention can be mixed with conventional pharmaceutical carriers and excipients and used in the form of solutions, emulsions, tablets, capsules, soft gels, elixirs, suspensions, syrups, wafers and the like. The compositions comprising a compound of the present invention will contain from about 0.1% to about 99.9%, about 1% to about 98%, about 5% to about 95%, about 10% to about 80% or about 15% to about 60% by weight of the active compound.

The pharmaceutical preparations disclosed herein are prepared in accordance with standard procedures and are administered at dosages that are selected to reduce, prevent, or eliminate cancer. (See, e.g., *Remington's Pharmaceutical Sciences*, Mack Publishing Company, Easton, Pa.; and Goodman and Gilman, *Pharmaceutical Basis of Therapeutics*, Pergamon Press, New York, N.Y., the contents of which are incorporated herein by reference, for a general description of the methods for administering various agents for human therapy).

As used herein, the term "unit dosage" refers to physically discrete units suitable as unitary dosages for human subjects and other mammals, each unit containing a predetermined quantity of farnesyl dibenzodiazepinone calculated to produce the desired therapeutic effect, in association with a suitable pharmaceutically acceptable carriers. In one embodiment, the unit dosage contains from 10 to 3000 mg of active ingredient. In another embodiment, the unit dosage contains 20 to 1000 mg of active ingredient. The compositions of the present invention can be delivered using controlled (e.g., capsules) or sustained release delivery systems (e.g., bioerodable matrices). Exemplary delayed release delivery systems for drug delivery that are suitable for administration of the compositions of the invention are described in U.S. Pat. No. 4,452,775 (issued to Kent), U.S. Pat. No. 5,039,660 (issued to Leonard), and U.S. Pat. No. 3,854,480 (issued to Zaffaroni).

The pharmaceutically-acceptable compositions of the present invention comprise one or more compounds of the present invention in association with one or more non-toxic, pharmaceutically-acceptable carriers and/or diluents and/or adjuvants and/or excipients, collectively referred to herein as "carrier" materials, and if desired other active ingredients. Pharmaceutically acceptable carriers include, for example, solvents, vehicles or medium such as saline, buffered saline, dextrose, water, glycerol, ethanol, propylene glycol, polysorbate 80 (Tween-80™), poly(ethylene) glycol 300 and 400 (PEG 300 and 400), PEGylated castor oil (E.g. Cremophor EL), poloxamer 407 and 188, hydrophobic carriers, and combinations thereof. Hydrophobic carriers include, for example, fat emulsions, lipids, PEGylated phopholids, polymer matrices, biocompatible polymers, liposphere, vesicles, particles, and liposomes. The term specifically excludes cell culture medium.

Excipients or additives included in a formulation have different purposes depending, for example on the nature of the drug, and the mode of administration. Examples of generally used excipients include, without limitation: stabilizing agents, solubilizing agents and surfactants, buffers, antioxidants and preservatives, tonicity agents, bulking agents, lubricating agents, emulsifiers, suspending or viscosity agents, inert diluents, fillers, disintegrating agents, binding agents, wetting agents, lubricating agents, antibacterials, chelating agents, sweetners, perfuming agents, flavouring agents, coloring agents, administration aids, and combinations thereof.

The compositions may contain common carriers and excipients, such as cornstarch or gelatin, lactose, sucrose, microcrystalline cellulose, kaolin, mannitol, dicalcium phosphate, sodium chloride and alginic acid. The compositions may contain crosarmellose sodium, microcrystalline cellulose, sodium starch glycolate and alginic acid.

Formulations for parenteral administration can be in the form of aqueous or non-aqueous isotonic sterile injection solutions, suspensions or fat emulsions, comprising a compound of this invention, or a pharmaceutically acceptable salt or prodrug thereof. The parenteral form used for injection must be fluid to the extent that easy syringability exists. These solutions or suspensions can be prepared from sterile concentrated liquids, powders or granules. The compounds can be dissolved in a carrier such as a solvent or vehicle, for example, polyethylene glycol, propylene glycol, ethanol, corn oil, benzyl alcohol, glycofurol, N,N-dimethylacetamide, N-methylpyrrolidone, glycerine, saline, dextrose, water, glycerol, hydrophobic carriers, and combinations thereof.

Excipients used in parenteral preparations also include, without limitation, stabilizing agents (e.g. carbohydrates, amino acids and polysorbates), solubilizing agents (e.g. cetrimide, sodium docusate, glyceryl monooleate, polyvinylpyrolidone (PVP) and polyethylene glycol (PEG)) and surfactants (e.g. polysorbates, tocopherol PEG succinate, poloxamer and Cremophor™), buffers (e.g. acetates, citrates, phosphates, tartrates, lactates, succinates, amino acids and the like), antioxidants and preservatives (e.g. BHA, BHT, gentisic acids, vitamin E, ascorbic acid and sulfur containing agents such as sulfites, bisulfites, metabisulfites, thioglycerols, thioglycolates and the like), tonicity agents (for adjusting physiological compatibility), suspending or viscosity agents, antibacterials (e.g. thimersol, benzethonium chloride, benzalkonium chloride, phenol, cresol and chlorobutanol), chelating agents, and administration aids (e.g. local anesthetics, anti-inflammatory agents, anti-clotting agents, vaso-constrictors for prolongation and agents that increase tissue permeability), and combinations thereof.

Parenteral formulations using hydrophobic carriers include, for example, fat emulsions and formulations containing lipids, liposheres, vesicles, particles and liposomes. Fat emulsions include in addition to the above-mentioned excipients, a lipid and an aqueous phase, and additives such as emulsifiers (e.g. phospholipids, poloxamers, polysorbates, and polyoxyethylene castor oil), and osmotic agents (e.g. sodium chloride, glycerol, sorbitol, xylitol and glucose). Liposomes include natural or derived phospholipids and optionally stabilizing agents such as cholesterol.

In another embodiment, the parenteral unit dosage form of the compound can be a ready-to-use solution of the compound or a salt thereof in a suitable carrier in sterile, hermetically sealed ampoules or in sterile pre-loaded syringes. The suitable carrier optionally comprises any of the above-mentioned excipients.

Alternatively, the unit dosage for of the compound of the present invention can be in a concentrated liquid, powder or granular form for ex tempore reconstitution in the appropriate pharmaceutically acceptable carrier at the time of delivery. In addition the above-mentioned excipients, powder forms optionally include bulking agents (e.g. mannitol, glycine, lactose, sucrose, trehalose, dextran, hydroxyethyl starch, ficoll and gelatin), and cryo or lyoprotectants.

For example, in intravenous (IV) use, a sterile formulation of the compound of Formula I and optionally one or more additives, including solubilizers or surfactants, can be dissolved or suspended in any of the commonly used intravenous fluids and administered by infusion. Intravenous fluids include, without limitation, physiological saline, phosphate buffered saline, 5% glucose or Ringer's™ solution.

In another example, in intramuscular preparations, a sterile formulation of the compound of the present invention or suitable soluble salts or prodrugs forming the compound, can be dissolved and administered in a pharmaceutical diluent such as Water-for-lnjection (WFI), physiological saline or 5% glucose. A suitable insoluble form of the compound may be prepared and administered as a suspension in an aqueous base or a pharmaceutically acceptable oil base, e.g. an ester of a long chain fatty acid such as ethyl oleate.

For oral use, solid formulations such as tablets and capsules are particularly useful. Sustained released or enterically coated preparations may also be devised. For pediatric and geriatric applications, suspension, syrups and chewable tablets are especially suitable. For oral administration, the pharmaceutical compositions are in the form of, for example, tablets, capsules, suspensions or liquid syrups or elixirs, wafers and the like. For general oral administration, excipient or additives include, but are not limited to inert diluents, fillers, disintegrating agents, binding agents, wetting agents, lubricating agents, sweetening agents, flavoring agents, coloring agents and preservatives.

The oral pharmaceutical composition is preferably made in the form of a unit dosage containing a therapeutically-effective amount of the active ingredient. Examples of such dosage units are tablets and capsules. For therapeutic purposes, the tablets and capsules which can contain, in addition to the active ingredient, conventional carriers such as: inert diluents (e.g., sodium and calcium carbonate, sodium and calcium phosphate, and lactose), binding agents (e.g., acacia gum, starch, gelatin, sucrose, polyvinylpyrrolidone (Providone), sorbitol, or tragacanth methylcellulose, sodium carboxymethylcellulose, hydroxypropyl methylcellulose, and ethylcellulose), fillers (e.g., calcium phosphate, glycine, lactose, maize-starch, sorbitol, or sucrose), lubricants or lubricating agents (e.g., magnesium stearate or other metallic stearates, stearic acid, polyethylene glycol, waxes, oils, silica and colloical silica, silicon fluid or talc), disintegrants or disintegrating agents (e.g., potato starch, corn starch and alginic acid), flavouring, coloring agents, or acceptable wetting agents. Carriers may also include coating excipients such as glyceryl monostearate or glyceryl distearate, to delay absorption in the gastrointestinal tract.

Oral liquid preparations, generally in the form of aqueous or oily solutions, suspensions, emulsions, syrups or elixirs, may contain conventional additives such as suspending agents, emulsifying agents, non-aqueous agents, preservatives, coloring agents and flavoring agents. Examples of additives for liquid preparations include acacia, almond oil, ethyl alcohol, fractionated coconut oil, gelatin, glucose syrup, glycerin, hydrogenated edible fats, lecithin, methyl cellulose, methyl or propyl para-hydroxybenzoate, propylene glycol, sorbitol, or sorbic acid.

For both liquid and solid oral preparations, flavoring agents such as peppermint, oil of wintergreen, cherry, grape, fruit flavoring or the like can also be used. It may also be desirable to add a coloring agent to make the dosage form more aesthetic in appearance or to help identify the product. For topical use the compounds of present invention can also be prepared in suitable forms to be applied to the skin, or mucus membranes of the nose and throat, and can take the form of creams, ointments, liquid sprays or inhalants, lozenges, or throat paints. Such topical formulations further can include chemical compounds such as dimethylsulfoxide (DMSO) to facilitate surface penetration of the active ingredient. For application to the eyes or ears, the compounds of the present invention can be presented in liquid or semi-liquid form formulated in hydrophobic or hydrophilic bases as ointments, creams, lotions, paints or powders. For rectal administration the compounds of the present invention can be administered in the form of suppositories admixed with conventional carriers such as cocoa butter, wax or other glyceride.

V. Methods for Treating Neoplasms

In one aspect, the invention relates to a method for inhibiting growth and/or proliferation of cancer cells in a mammal. In another aspect, the invention provides a method for treating neoplasms in a mammal. Mammals include ungulates (e.g. sheeps, goats, cows, horses, pigs), and non-ungulates, including rodents, felines, canines and primates (i.e. human and non-human primates). In a preferred embodiment, the mammal is a human.

Although not wishing to be bound by any particular theory, the farnesyl dibenzodiazepinone compounds of the present invention may exert their anticancer effects, at least in part, through interaction with the peripheral benzodiazepine receptor (PBR). PBR is an evolutionarily conserved 18-kDa protein, which is present in all tissues but highly expressed in steroid producing tissues and cancers, and has been associated with numerous biological functions, including regulation of apoptosis, regulation of cell proliferation, and stimulation of steroidogenesis. PBR is a critical component of the mitochondrial permeability transition pore (MPTP), a multiprotein complex located at the contact site between inner and outer mitochondrial membranes, which is intimately involved in the intiation and regulation of apoptosis. Moreover, PBR ligands have been shown to modulate MPTP and apoptotic response (see Carayon et al., *Blood* (1995) 87(8):3170; Hirsch et al., *Experimental Cell. Research* (1998) 241 no 2:426-434; and Bono et al., *Biochem. Biophys. Res. Comm.* (1999) 265:457). Several recent reports have linked PBR and cancer based on alteration of PBR expression in tumor cells and PBR-dependent apoptotic modulations. Some of the highest densities of PBR are observed in neoplastic tissues and cell lines. Ovarian, hepatic and colon carcinomas, adenocarcinoma, glioma and breast cancer cells all show increased PBR densities relative to untranformed tissues (see Miettinen et al., *Cancer Res.* (1995) 55:2691-2695; Katz et al., *Clin. Sci.* (1990) 78:155; Katz et al., *Oncology* (1990) 47:139; and Venturini et al., *Life Sci.* (1999) 65:2223).

PBR ligands, both endogenous and synthetic, have been shown to have antiproliferative and pro-apoptotic properties. For example, the therapeutic potency of porphrins for the treatment of skin, bladder and lung cancers are reportedly linked to their affinities to PBR, and the sentitivity of tumor cell lines to photodynamic therapy reportedly parallel their PBR densities (Verma et al., *Mol. Med.* (1998) 4(1):40; Kupczyk-Subotkowska et al., *J. Med. Chem.* (1997) 40(11): 1726; and Guo et al., *Cancer Chemother. Pharmacol.* (2001) 48(2):169). In addition to indirect PBR-based anticancer therapies, some PBR ligands have direct anticancer properties, including apoptotic and cell cycle inhibitor properties (Wang et al., *Proc. Natl. Acad. Sci. USA* (1984) 81:753; Landau et al., *J. Biochem. Pharmacol.* (1998) 56:1029; and Stoebner et al., *Cell Death Differ.* (2001) 8(7):747). Similarly, the farnesyl dibenzodiazepinone compounds of the present invention, in particular ECO-4601, have been shown to bind to the PBR and inhibit cellular proliferation in a panel of different types of tumor cell lines, including low and high-grade gliomas. ECO-4601 also increases expression of several genes involved in the regulation of apoptosis and signal transduction, as well as genes involved in steroid biosynthesis. Since human glioblastomas have an increased density of PBR compared with normal human brain, ECO-4601's anticancer activity is believed to be via interaction with the PBR. ECO-4601 has been shown to penetrate into brain tissues.

Alternatively, or in addition, the farnesyl dibenzodiazepinone compounds of the invention may have chemosensitizing or multidrug resistance modulating activity, as has been reported for other PBR ligands. For example, a non-cytotoxic dose of PK11195 increased the efficacy of a daunorubicin treatment on human multidrug-resistant leukemia cells in vitro and in vivo (Jakubikova et al., *Neoplasma* (2002) 49(4):231; and Decaudin et al., *Cancer Res.* (2002) 62(5): 1388). Thus, the farnesyl dibenzodiazepinone compounds, like other PBR ligands, may inhibit the expression or activity of multi-drug resistance (MDR)-associated protein (MDRP) or multi-drug resistance protein-1 (MDR1). "Multi-drug resistance" (MDR) broadly refers to a pattern of resistance to a variety of chemotherapeutic drugs with unrelated chemical structures and different mechanisms of action. Although the etiology of MDR is multifactorial, the overexpression of P-glycoprotein (Pgp), a membrane protein that mediates the transport of MDR drugs, remains the most common alteration underlying MDR in laboratory models (Childs, S., *Imp. Adv. Oncol.* (1994) 21-36). Moreover, expression of Pgp has been linked to the development of MDR in human cancer, particularly in the leukemias, lymphomas, multiple myeloma, neuroblastoma, and soft tissue sarcoma (Fan., D., et al., *Reversal of Multidrug Resistance in Cancer*, ed. Kellen, J. A. (1993) (CRC Press, Boca Raton, Fla.), pp. 93-125). Recent studies showed that tumor cells expressing MDRP (Cole, S. P., et al., *Science* (1992) 258: 1650-1654) and lung resistance protein (LRP) (Scheffer, G. L., et al., *Nat. Med.* (1995)1:578-582) and mutation of DNA topoisomerase II (Beck, W. T., *J. Natl. Cancer Inst.* (1989) 81:1683-1685) also may render MDR.

While the above suggests that the farnesyl dibenzodiazepinones of the invention may exert anticancer effects via interaction with the PBR, the mechanism of action may also be due, at least in part, to some as yet undefined mechanism or pathway. Alternatively or in addition to PBR, the farnesyl dibenzodiazepinone compounds of the present invention may bind to or interact with other cancer-associated proteins and polypeptides, including, without limitation, polypeptides encoded by oncogenes, polypeptides that induce angiogenesis, proteins involved in metastasizing and/or invasive processes, and proteases that regulate apoptosis and the cell cycle. Regardless of the mechanism of action, the farnesyl dibenzodiazepinone compounds of the invention have been demonstrated to exhibit anti-cancer activity both in vitro and in vivo. Based on these discoveries, applicants have developed methods for treating neoplasms.

As used herein, the terms "neoplasm", "neoplastic disorder", "neoplasia" "cancer," "tumor" and "proliferative disorder" refer to cells having the capacity for autonomous growth, i.e., an abnormal state of condition characterized by rapidly proliferating cell growth which generally forms a distinct mass that show partial or total lack of structural organization and functional coordination with normal tissue. The terms are meant to encompass hematopoietic neoplasms (e.g. lymphomas or leukemias) as well as solid neoplasms (e.g. sarcomas or carcinomas), including all types of pre-cancerous and cancerous growths, or oncogenic processes, metastatic tissues or malignantly transformed cells, tissues, or organs, irrespective of histopathologic type or stage of invasiveness. Hematopoietic neoplasms are malignant tumors affecting hematopoietic structures (structures pertaining to the formation of blood cells) and components of the immune system, including leukemias (related to leukocytes (white blood cells) and their precursors in the blood and bone marrow) arising from myeloid, lymphoid or erythroid lineages, and lymphomas (relates to lymphocytes). Solid neoplasms include sarcomas, which are malignant neoplasms that originate from connective tissues such as muscle, cartilage, blood vessels, fibrous tissue, fat or bone. Solid neoplasms also include carcinomas, which are malignant neoplasms arising from epithelial structures (including external epithelia (e.g., skin and linings of the gastrointestinal tract, lungs, and cervix), and internal epithelia that line various glands (e.g., breast, pancreas, thyroid). Examples of neoplasms that are particularly susceptible to treatment by the methods of the invention include leukemia, and hepatocellular cancers, sarcoma, vascular endothelial cancers, breast carcers, central nervous system cancers (e.g. astrocytoma, gliosarcoma, neuroblastoma, oligodendroglioma and glioblastoma), prostate cancers, lung and bronchus cancers, larynx cancers, esophagus cancers, colon cancers, colorectal cancers, gastro-intestinal cancers, melanomas, ovarian and endometrial cancer, renal and bladder cancer, liver cancer, endocrine cancer (e.g. thyroid), and pancreatic cancer.

The farnesyl dibenzodiazepinone that binds or otherwise interacts with the target protein associated with cancer, or one expressed at higher levels in cancer cells compared to normal cells, is brought into contact with or introduced into a cancerous cell or tissue. In general, the methods of the invention for delivering the compositions of the invention in vivo utilize art-recognized protocols for delivering therapeutic agents with the only substantial procedural modification being the substitution of the farnesyl dibenzodiazepinone of the present invention for the therapeutic agent in the art-recognized protocols. The route by which the farnesyl dibenzodiazepinone is administered, as well as the formulation, carrier or vehicle will depend on the location as well as the type of the neoplasm. A wide variety of administration routes can be employed. The farnesyl dibenzodiazepinone may be administered by intravenous or intraperitoneal infusion or injection. For example, for a solid neoplasm that is accessible, the farnesyl dibenzodiazepinone may be administered by injection directly into the neoplasm. For a hematopoietic neoplasm the farnesyl dibenzodiazepinone may be administered intravenously or intravascularly. For neoplasms that are not easily accessible within the body, such as metastases or brain tumors, the farnesyl dibenzodiazepinone may be administered in a manner such that it can be transported systemically through the body of the mammal and thereby reach the neoplasm and distant metastases for example intrathecally, intravenously or intramuscularly or orally. Alternatively, the farnesyl dibenzodiazepinone can be administered directly to the tumor. The farnesyl dibenzodiazepinone can also be administered subcutaneously, intraperitoneally, topically (for example for melanoma), rectally (for example colorectal neoplasm) vaginally (for example for cervical or vaginal neoplasm), nasally or by inhalation spray (for example for lung neoplasm).

The farnesyl dibenzodiazepinone is administered in an amount that is sufficient to inhibit the growth or proliferation of a neoplastic cell, or to treat a neoplastic disorder. The term "inhibition" refers to suppression, killing, stasis, or destruction of cancer cells. The inhibition of mammalian cancer cell growth according to this method can be monitored in several ways. Cancer cells grown in vitro can be treated with the compound and monitored for growth or death relative to the same cells cultured in the absence of the compound. A cessation of growth or a slowing of the growth rate (i.e., the doubling rate), e.g., by 50% or more at 100 micromolar, is indicative of cancer cell inhibition (see Anticancer Drug Development Guide: preclinical screening, clinical trials and approval; B. A. Teicher and P. A. Andrews, ed., 2004, Humana Press, Totowa, N.J.). Alternatively, cancer cell inhibition can be monitored by administering the compound to an animal model of the cancer of interest. Examples of experimental non-human animal cancer models are known in the art and described below and in the examples herein. A cessation of tumor growth (i.e., no further increase in size) or a reduction in tumor size (i.e., tumor volumeby least a 58%) in animals treated with the compound relative to tumors in control animals not treated with the compound is indicative of significant tumor growth inhibition (see Anticancer Drug Development Guide: preclinical screening, clinical trials and approval; B. A. Teicher and P. A. Andrews, ed., 2004, Humana Press, Totowa, N.J.).

The term "treatment" refers to the application or administration of a farnesyl dibenzodiazepinone to a mammal, or application or administration of a farnesyl dibenzodiazepinone to an isolated tissue or cell line from a mammal, who has a neoplastic disorder, a symptom of a neoplastic disorder or a predisposition toward a neoplastic disorder, with the purpose to cure, heal, alleviate, relieve, alter, ameliorate, improve, or control the disorder, the symptoms of disorder, or the predisposition toward disorder. The term "treating" is defined as administering, to a mammal, an amount of a farnesyl dibenzodiazepinone sufficient to result in the prevention, reduction or elimination of neoplastic cells in a mammal ("therapeutically effective amount"). The therapeutically effective amount and timing of dosage will be determined on an individual basis and may be based, at least in part, on consideration of the age, body weight, sex, diet and general health of the recipient subject, on the nature and severity of the disease condition, and on previous treatments and other diseases present. Other factors also include the route and frequency of administration, the activity of the administered compound, the metabolic stability, length of action and excretion of the compound, drug combination, the tolerance of the recipient subject to the compound and the type of neoplasm or proliferative disorder. In one embodiment, a therapeutically effective amount of the compound is in the range of about 0.01 to about 750 mg/kg of body weight of the mammal. In another embodiment, the therapeutically effective amount is in the range of about 0.01 to about 300 mg/kg body weight per day. In yet another embodiment, the therapeutically effective amount is in the range of 10 to about 50 mg/kg body weight per day. The therapeutically effective doses of the above embodiments may also be expressed in milligrams per square meter (mg/m$^2$) in the case of a human patient. Conversion factors for different mammalian species may be found in: Freireich et al, Quantitative comparison of toxicity of anticancer agents in mouse, rat, dog, monkey and man, Cancer Chemoth. Report, 1966, 50(4): 219-244).

To monitor the efficacy of tumor treatment in a human, tumor size and/or tumor morphology is measured before and after initiation of the treatment, and treatment is considered effective if either the tumor size ceases further growth, or if the tumor is reduced in size, e.g., by at least 10% or more (e.g., 20%, 30%, 40%, 50%, 60%, 70%, 80%, 90% or even 100%, that is, the absence of the tumor). Prolongation of survival, time-to-disease progression, partial response and objective response rate are surrogate measures of clinical activity of the investigational agent. Tumor shrinkage is considered to be one treatment-specific response. This system is limited by the requirement that patients have visceral masses that are amenable to accurate measurement. Methods of determining the size of a tumor in vivo vary with the type of tumor, and include, for example, various imaging techniques well known to those in the medical imaging or oncology fields (MRI, CAT, PET, etc.), as well as histological techniques and flow cytometry. For certain types of cancer, evaluation of serum tumor markers are also used to evaluate response (eg prostate-specific antigen (PSA) for prostate cancer, and carcino-embryonic antigen (CEA), for colon cancer). Other methods of monitoring cancer growth include cell counts (e.g. in leukemias) in blood or relief in bone pain (e.g. prostate cancer).

The farnesyl dibenzodiazepinone compound may be administered once daily, or the compound may be administered as two, three, four, or more sub-doses at appropriate intervals throughout the day. In that case, the farnesyl dibenzodiazepinone compound contained in each sub-dose must be correspondingly smaller in order to achieve the total daily dosage. The dosage unit can also be compounded for delivery over several days, e.g., using a conventional sustained release formulation which provides sustained release of the farnesyl dibenzodiazepinone compound over a several day period. Sustained release formulations are well known in the art. In this embodiment, the dosage unit contains a corresponding multiple of the daily dose. The effective dose can be administered either as a single administration event (e.g., a bolus injection) or as a slow injection or infusion, e.g. over 30 minutes to about 24 hours. The compound may be administered as a treatment, for up to 30 days. Moreover, treatment of a subject with a therapeutically effective amount of a composition can include a single treatment or a series of treatments. Estimates of effective dosages, toxicities and in vivo half-lives for the farnesyl dibenzodiazepinone compounds encompassed by the invention can be made using conventional methodologies or on the basis of in vivo testing using an appropriate animal model.

The farnesyl dibenzodiazepinone may be administered in conjunction with or in addition to known anticancer compounds or chemotherapeutic agents. Such agents include, but are not limited to, 5-flurouracil, mitomycin C, methotrexate, hydroxyurea, cyclophosphamide, dacarbazine, mitoxantrone, anthracyclins (Epirubicin and Doxurubicin), etopside, pregnasome, platinum compounds such as carboplatin and cisplatin, taxanes such as taxol and taxotere; hormone therapies such as tamoxifen and anti-estrogens; antibodies to receptors, such as herceptin and Iressa; aromatase inhibitors, progestational agents and LHRH analogs; biological response modifiers such as IL2 and interferons; multidrug reversing agents such as the cyclosporin analog PSC 833.

Toxicity and therapeutic efficacy of farnesyl dibenzodiazepinone compounds can be determined by standard pharmaceutical procedures in cell cultures or experimental animals. Therapeutic efficacy is determined in animal models as described above and in the examples herein. Toxicity studies are done to determine the lethal dose for 10% of tested animals (LD10). Animals are treated at the maximum tolerated dose (MTD): the highest dose not producing mortality or greater than 20% body weight loss. The effective dose (ED) is related to the MTD in a given tumor model to determine the therapeutic index of the compound. A therapeutic index (MTD/ED) close to 1.0 has been found to be acceptable for some chemotherapeutic drugs, a preferred therapeutic index for classical chemotheapeutic drugs is 1.25 or higher.

The data obtained from cell culture assays and animal studies can be used in formulating a range of dosage for use in humans. The dosage of compositions of the invention will generally be within a range of circulating concentrations that include the MTD. The dosage may vary within this range depending upon the dosage form employed and the route of administration utilized. For any compound used in the method of the invention, the therapeutically effective dose can be estimated initially from cell culture assays. A dose may be formulated in animal models to achieve a circulating plasma concentration range of the compound. Such information can be used to more accurately determine useful doses in humans. Levels in plasma may be measured, for example, by high performance liquid chromatography.

Animal models to determine antitumor efficacy of a compound are generally carried out in mice. Either murine tumor cells are inoculated subcutaneously into the hind flank of mice from the same species (syngeneic models) or human tumor cells are inoculated subcutaneously into the hind flank of severe combined immune deficient (SCID) mice or other immune deficient mouse (nude mice) (xenograft models).

Advances in mouse genetics have generated a number of mouse models for the study of various human diseases including cancer. The MMHCC (Mouse models of Human Cancer Consortium) web page (emice.nci.nih.gov), sponsored by the National Cancer Institute, provides disease-site-specific compendium of known cancer models, and has links to the searchable Cancer Models Database (cancermodels.nci.nih.gov), as well as the NCI-MMHCC mouse repository. Mouse repositories can also be found at: The Jackson Laboratory, Charles River Laboratories, Taconic, Harlan, Mutant Mouse Regional Resource Centers (MMRRC) National Network and at the European Mouse Mutant Archive. Such models may be used for in vivo testing of farnesyl dibenzodiazepinone compounds, as well as for determining a therapeutically effective dose.

Unless otherwise indicated, all numbers expressing quantities of ingredients, properties such as molecular weight, reaction conditions, $IC_{50}$ and so forth used in the specification and claims are to be understood as being modified in all instances by the term "about." Accordingly, unless indicated to the contrary, the numerical parameters set forth in the present specification and attached claims are approximations. At the very least, and not as an attempt to limit the application of the doctrine of equivalents to the scope of the claims, each numerical parameter should at least be construed in light of the number of significant figures and by applying ordinary rounding techniques. Notwithstanding that the numerical ranges and parameters setting forth the broad scope of the invention are approximations, the numerical values set in the examples, Tables and Figures are reported as precisely as possible. Any numerical values may inherently contain certain errors resulting from variations in experiments, testing measurements, statistical analyses and such.

Unless otherwise defined, all technical and scientific terms used herein have the same meaning as commonly understood by one of ordinary skill in the art to which this invention belongs. Although methods and materials similar or equivalent to those described herein can be used in the practice or testing of the present invention, suitable methods and materials are described below. All publications, patent applications, patents, and other references mentioned herein are incorporated by reference in their entirety. In case of conflict, the present specification, including definitions, will control. In addition, the materials, methods, and examples are illustrative only and not intended to be limiting.

EXAMPLES

Example 1

Production of the Compound of Formula I

The compound of Formula I was isolated from the fermentation broth of either strains of *Micromonospora* [S01] 046 or 046-ECO11respectively having IDAC 231203-01 and 070303-01 accession numbers (International Depository Authority of Canada (IDAC), Bureau of Microbiology, Health Canada, 1015 Arlington Street, Winnipeg, Manitoba, Canada, R3E 3R2). The compound of Formula I was produced and isolated as described in published United States Patent Application US 2005/0043297 (WO 2004/065591 in August 2004), incorporated herein by reference in their entirety.

Example 2

Elucidation of the Structure of Compound of Formula I

The structure of the compound of Formula I was derived from mass spectrometry data and spectroscopic data, including ultraviolet (UV), and nuclear magnetic resonance (NMR), Fournier Transform Infrared (FTIR) spectroscopy. Mass was determined by electrospray mass spectrometry to be 462.6 g/mol, UV spectra in acetonitrile showed a maximum peak at 221 nm with a shoulder at 290 nm. NMR data of the compound of Formula I were collected in MeOH-d4, including proton, and multidimensional pulse sequences gDQCOSY, gHSQC, gHMBC, and NOESY.

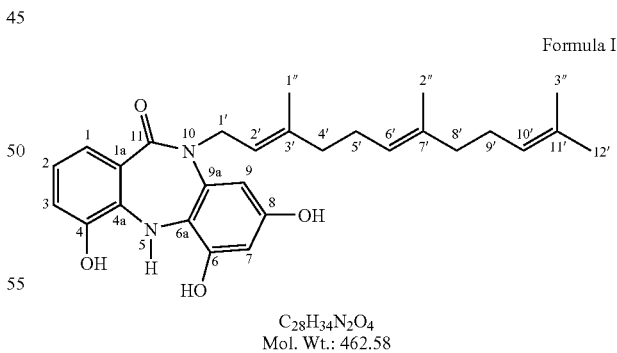

Formula I $C_{28}H_{34}N_2O_4$
Mol. Wt.: 462.58

A number of cross peaks in the 2D spectra of the compound of Formula I are key in the structural determination. For example, the farnesyl chain is placed on the amide nitrogen by a strong cross peak between the proton signal of the terminal methylene of that chain at 4.52 ppm and the amide carbonyl carbon at 170 ppm in the gHMBC experiment. This conclusion is confirmed by a cross peak in the NOESY spectrum between the same methylene signals at 4.52 ppm and the aromatic proton signal at 6.25 ppm from one of the two protons of the tetra substituted benzenoid ring. nt of proton and carbon signals are shown in Table 1.

TABLE 1

$^1H$ and $^{13}C$ NMR ($\delta_H$, ppm) Data of Compound 1 in MeOH—$D_4$

| Assignment | $^1H$ | $^{13}C$ | Group |
|---|---|---|---|
| 1 | 7.15 | 122.3 | CH |
| 1a | — | 125.0 | C |
| 2 | 6.74 | 121.0 | CH |
| 3 | 6.83 | 116.9 | CH |
| 4 | — | 146.0 | C—OH |
| 4a | — | 142.0 | C |
| 6 | — | 148.2 | C—OH |
| 6a | — | 126.0 | C |
| 7 | 6.20 | 100.0 | CH |
| 8 | — | 153.0 | C—OH |
| 9 | 6.25 | 101.0 | CH |
| 9a | — | 135.0 | C |
| 11 | — | 170.0 | C(O) |
| 1' | 4.52 | 48.7 | $CH_2$ |
| 2' | 5.35 | 121.1 | CH |
| 3' | — | 138.5 | C |
| 4' | 2.03 | 39.5 | $CH_2$ |
| 5' | 2.08 | 26.7 | $CH_2$ |
| 6' | 5.09 | 124.1 | CH |
| 7' | — | 135.0 | C |
| 8' | 1.95 | 39.6 | $CH_2$ |
| 9' | 2.02 | 26.3 | $CH_2$ |
| 10' | 5.06 | 124.4 | CH |
| 11' | — | 130.9 | C |
| 12' | 1.64 | 24.8 | $CH_3$ |
| 1" | 1.72 | 15.5 | $CH_3$ |
| 2" | 1.59 | 14.9 | $CH_3$ |
| 3" | 1.55 | 16.5 | $CH_3$ |

Based on the mass spectrometry, UV and NMR spectroscopy data, the structure of the compound was determined to be the structure of Formula I.

Example 3

Anticancer Activity in Vitro Against Human and Animal Tumor Cell Lines from Various Tissues Culture conditions: The cell lines listed in Table 2 were used to characterize the cytotoxicity of the compound of Formula I against human and mouse tumor cell lines. These cell lines were shown to be free of mycoplasma infection and were maintained on the appropriate media (Table 2) supplemented with 10% heat-inactivated fetal bovine serum and 1% penicillin-streptomycin, under 5% $CO_2$ at 37° C. Cells were passaged twice to three times per week. Viability was examined by staining with 0.25% trypan blue and only flasks where cell viability was >95% were used for this study.

Cell lines amplification and plating: Tumor cells were seeded ($1-3 \times 10^3$ cells per 100 μL) in 96-wells flat bottom microtiter plates and incubated at 37° C. and 5% $CO_2$ for 16 hrs before treatment in drug-free medium supplemented with 10% serum.

Evaluation of inhibitory activity on cell proliferation: Cells were incubated for 96 hrs with 6 $\log_{10}$-fold concentrations of the test substance starting at 10 μg/ml (~20 μM). The test substance stock solution (5 mg/mL) was initially diluted at 1/500 fold in medium supplemented with serum. Other concentrations were then obtained from 1/10 fold successive dilutions in the same supplemented medium. Cell survival was evaluated 96 h later by replacing the culture media with 150 μL fresh medium containing 10 mM 4-(2-hydroxyethyl)-1-piperazineethanesulfonic acid buffer, pH 7.4. Next, 50 μL of 2.5 mg/mL of 3-(4,5-dimethylthiazo-2-yl)-2,5-diphenyltetrazolium bromide (MTT) in phosphate buffer solution, pH 7.4, was added. After 3-4 h of incubation at 37° C., the medium and soluble MTT was removed, and 200 μL of dimethylsulfoxide was added to dissolve the precipitate of reduced MTT followed by addition of 25 μL glycine buffer (0.1 M glycine plus 0.1 M NaCl, pH 10.5). The absorbance was determined at 570 nm with a microplate reader. Results were expressed as the concentration of drug which inhibits 50% of the cells compared to the untreated control wells ($IC_{50}$). The $IC_{50}$ values shown in Table 2 demonstrated a pharmacologically relevant cytotoxic activity of the compound of Formula I against a variety of cancer types such as leukemias, melanomas, pancreatic and breast carcinomas.

TABLE 2

| Cell lines | Type | Origin | Source | Culture medium | $IC_{50}$ ($\times 10^{-6}$ M) |
|---|---|---|---|---|---|
| K562 | Leukemia myelogeneous | Human | ATCC | RPMI 1640 | 8.6 |
| P388 | Leukemia | Mouse | ATCC | RPMI 1640 | 10.9 |
| I83 | Leukemia | Human | ATCC | RPMI 1640 | 2.7 |
| B16 (F10) | Melanoma | Mouse | ATCC | RPMI 1640 | 11.4 |
| SK-MEL 28 | Melanoma | Human | ATCC | RPMI 1640 | 14.0 |
| SK-MEL 28$^{VEGF}$ | Melanoma (expressing VEGF) | Human | ATCC | RPMI 1640 | 14.3 |
| SK-MEL-1 | Melanoma | Human | ATCC | EMEM 1% non-essential amino acid 1% Sodium puryvate | 14.1 |
| Panc 96 | Pancreatic carcinoma | Human | ATCC | RPMI 1% Sodium puryvate | 12.5 |
| Panc 10.05 | Pancreatic carcinoma | Human | ATCC | RPMI 1% Sodium puryvate Insulin | 14.2 |
| MCF-7 | Breast adenocarcinoma | Human | ATCC | RPMI 1640 | 9.7 |

Example 4

Anticancer Activity in Vitro Against Various Human Tumor Cell Lines from the U.S. National Cancer Institute Panel A study measuring the in vitro antitumor activity of the compound of Formula I was performed by the National Cancer Institute (National Institutes of Health, Bethesda, Md., USA) against panel of human cancer cell lines in order to determine the compound of Formula I concentrations needed to obtain a 50% inhibition of cell proliferation ($GI_{50}$). The operation of this unique screen utilizes 60 different human tumor cell lines, representing leukemia, melanoma and cancers of the lung, colon, brain, ovary, breast, prostate, and kidney.

Culture conditions and plating: The human tumor cell lines of the cancer-screening panel were grown in RPMI 1640 medium containing 5% fetal bovine serum and 2 mM L-glutamine. For a typical screening experiment, cells were inoculated into 96 well microtiter plates in 100 μL at plating densities ranging from 5,000 to 40,000 cells/well depending on the doubling time of individual cell lines (Table 3). After cell inoculation, the microtiter plates were incubated at 37° C., 5% $CO_2$, 95% air and 100% relative humidity for 24 h prior to addition of experimental drugs. After 24 h, two plates of each cell line were fixed in situ with TCA, to represent a measurement of the cell population for each cell line at the time of drug addition (Tz).

Evaluation of inhibitory activity on cell proliferation: The compound of Formula I was provided as a lyophilized powder with an estimated purity of 90+%. The compound was stored at −20° C. until day of use. The compound of Formula I was solubilized in dimethyl sulfoxide at 400-fold the desired final maximum test concentration. At the time of drug addition, an aliquot of frozen concentrate was thawed and diluted to twice the desired final maximum test concentration with complete medium containing 50 μg/mL gentamicin. Additional four, 10-fold or ½ log serial dilutions were made to provide a total of five drug concentrations plus control. Aliquots of 100 μl of these different drug dilutions were added to the appropriate microtiter wells already containing 100 μl of medium, resulting in the required final drug concentrations ($8.0 \times 10^{-5}$ M to $8.0 \times 10^{-9}$ M).

Following drug addition, the plates were incubated for an additional 48 h at 37° C., 5% $CO_2$, 95% air, and 100% relative humidity. For adherent cells, the assay was terminated by the addition of cold TCA. Cells were fixed in situ by the gentle addition of 50 μl of cold 50% (w/v) TCA (final concentration, 10% TCA) and incubated for 60 minutes at 4° C. Supernatants were discarded, and the plates were washed with tap water and air-dried. Sulforhodamine B (SRB) solution (100 μl) at 0.4% (w/v) in 1% acetic acid was added to each well, and plates were incubated for 10 minutes at room temperature. After staining, unbound dye was removed by washing with 1% acetic acid and the plates were air-dried. Bound stain was subsequently solubilized with 10 mM trizma base, and the absorbance was read on an automated plate reader at a wavelength of 515 nm. For suspension cells, the methodology was the same except that the assay was terminated by fixing settled cells at the bottom of the wells by gently adding 50 μl of 80% TCA (final concentration, 16% TCA).

The growth inhibitory activity of the compound of Formula I was measured by NCI utilizing the $GI_{50}$ value, rather than the classical $IC_{50}$ value. The $GI_{50}$ value emphasizes the correction for the cell count at time zero and, using the seven absorbance measurements [time zero, (Tz), control growth, (C), and test growth in the presence of drug at the five concentration levels (Ti)], $GI_{50}$ is calculated as $[(Ti-Tz)/(C-Tz)] \times 100 = -50$, which is the drug concentration resulting in a 50% reduction in the net protein increase (as measured by SRB staining) in control cells during the drug incubation.

Result: The compound of Formula I shows a significant anticancer activity against several types of cancer as revealed by the NCI screening. Results of the screen are shown in Table 3, and more detailed results of activity against gliomas are shown in Example 5 (Table 4).

TABLE 3

| Cell Line Name | Type | Origin | Inoculation Density (number of cells/well) | $GI_{50}$ ($\times 10^{-6}$ M) |
|---|---|---|---|---|
| CCRF-CEM | Leukemia | Human | 40,000 | 1.08 |
| K-562 | Leukemia | Human | 5,000 | 1.43 |
| RPMI-8226 | Leukemia | Human | 20,000 | 3.15 |
| A549/ATCC | Non-Small Cell Lung | Human | 7,500 | 9.10 |
| EKVX | Non-Small Cell Lung | Human | 20,000 | 0.23 |
| HOP-62 | Non-Small Cell Lung | Human | 10,000 | 8.29 |
| NCI-H226 | Non-Small Cell Lung | Human | 20,000 | 2.00 |
| NCI-H23 | Non-Small Cell Lung | Human | 20,000 | 2.02 |
| NCI-H460 | Non-Small Cell Lung | Human | 7,500 | 13.60 |
| NCI-H522 | Non-Small Cell Lung | Human | 20,000 | 3.44 |
| COLO 205 | Colon | Human | 15,000 | 12.70 |
| HCT-116 | Colon | Human | 5,000 | 2.92 |
| HCT-15 | Colon | Human | 10,000 | 9.73 |
| HT29 | Colon | Human | 5,000 | 20.70 |
| SW-620 | Colon | Human | 10,000 | 2.72 |
| SF-268 | CNS | Human | 15,000 | 4.94 |
| SF-295 | CNS | Human | 10,000 | 12.70 |
| SF-539 | CNS | Human | 15,000 | 0.0075 |
| SNB-19 | CNS | Human | 15,000 | 2.90 |
| SNB-75 | CNS | Human | 20,000 | 7.71 |
| U251 | CNS | Human | 7,500 | 2.19 |
| LOX IMVI | Melanoma | Human | 7,500 | 4.53 |
| M14 | Melanoma | Human | 15,000 | 4.57 |
| SK-MEL-2 | Melanoma | Human | 20,000 | 25.0 |
| SK-MEL-28 | Melanoma | Human | 10,000 | 11.6 |
| SK-MEL-5 | Melanoma | Human | 10,000 | 7.80 |
| UACC-257 | Melanoma | Human | 20,000 | 2.31 |
| UACC-62 | Melanoma | Human | 10,000 | 1.55 |
| IGR-OV1 | Ovarian | Human | 10,000 | 3.11 |
| OVCAR-3 | Ovarian | Human | 10,000 | 13.50 |
| OVCAR-4 | Ovarian | Human | 15,000 | 9.67 |
| OVCAR-5 | Ovarian | Human | 20,000 | 2.81 |
| OVCAR-8 | Ovarian | Human | 10,000 | 2.65 |
| SK-OV-3 | Ovarian | Human | 20,000 | 4.00 |
| 786-0 | Renal | Human | 10,000 | 6.99 |
| A498 | Renal | Human | 25,000 | 22.30 |
| ACHN | Renal | Human | 10,000 | 3.10 |
| CAKI-1 | Renal | Human | 10,000 | 15.20 |
| RXF 393 | Renal | Human | 15,000 | 7.71 |
| SN12C | Renal | Human | 15,000 | 3.85 |
| UO-31 | Renal | Human | 15,000 | 19.70 |
| DU-145 | Prostate | Human | 10,000 | 3.56 |
| MCF7 | Breast | Human | 10,000 | 10.10 |
| NCI/ADR-RES | Breast | Human | 15,000 | 18.30 |
| MDA-MB-231/ATCC | Breast | Human | 20,000 | 2.72 |
| HS 578T | Breast | Human | 20,000 | 2.76 |
| MDA-MB-435 | Breast | Human | 15,000 | 15.30 |
| BT-549 | Breast | Human | 20,000 | 0.11 |
| T-47D | Breast | Human | 20,000 | 0.77 |

The results indicate that the compound of Formula I was effective against most of the human cancer cell lines that have been assayed in the NCI screening panel suggesting a broad anticancer activity against several types of human cancer.

Example 5

In Vitro Antiproliferative Study Against a Panel of Glioma Cell Lines

The anticancer activity of the compound of Formula I was evaluated using a panel of glioma cancer cell lines shown in Table 4, and the 50% inhibition of cell proliferation ($IC_{50}$) was determined.

Culture conditions: The cell lines listed in Table 4 were shown to be free of mycoplasma infection and were maintained on Dulbecco's modified Eagle medium (DMEM) supplemented with 10% heat-inactivated fetal bovine serum and 1% penicillin-streptomycin, under 5% $CO_2$ at 37° C. Cells were passaged once a week. Prior to use, the cells were detached from the culture flask by treating with trypsin for five to ten minutes. The cells were counted with a Neubauer glass slide and viability assessed by 0.25% trypan blue exclusion. Only flasks with >95% cell viability, were used in the study.

Cell lines amplification and plating: Cells, $5 \times 10^3$ cells per well in 100 µL drug-free medium supplemented with 10% serum, were plated in 96-well flat bottom microtiter plates and incubated at 37° C. for 48 hrs before treatment.

Evaluation of inhibitory activity on cell proliferation: Cells (in triplicate wells) were incubated 96 hrs with medium containing different concentrations of the compound of Formula I, starting at 5.0 µg/ml (10 µM). The compound was used in a solution of 1% DMSO in D-MEM or RPMI media (or other equivalent media). The concentrations of the compound of Formula I were as follows: 10 µM (5.0 µg/ml), 1 µM (0.50 µg/ml), 0.5 µM (0.25 µg/ml), 0.1 µM (0.050 µg/ml), 0.5 µM (0.025 µg/ml), 0.01 µM (0.0050 µg/ml), 0.001 µM (0.00050 µg/ml). Negative controls were cells treated with vehicle alone (1% DMSO in culture medium). Positive controls were cells treated with 4 to 6 increasing concentrations of cisplatin (CDDP) (data not shown).

At the end of the cell treatment, cell culture media was replaced with 150 µl of fresh medium containing 10 mM of 4-(2-hydroxyethyl)-1-piperazineethanesulfonic acid buffer, pH 7.4. Then 50 µl of 2.5 mg/ml of 3-(4,5-dimethylthiazo-2-yl)-2,5-diphenyltetrazolium bromide in PBS pH 7.4, were added to each well and the culture plates incubated for 4 hrs at 37° C. The resulting supernatant was removed and formazan crystals were dissolved with 200 µl of DMSO followed by 25 µl of glycine buffer (0.1 M glycine plus 0.1 M NaCl, pH 10.5). The optical density was read in each well using a single wavelength spectrophotometer plate reader at 570 nm. Results were expressed as the concentration of drug which inhibits 50% of the treated cells compared to the untreated controls ($IC_{50}$). Each of the cell lines was tested in at least 3 independent experiments.

Results shown in Table 4 confirmed the activity of the compound of Formula I against different brain cancer cell lines including gliosarcoma, which is the most malignant form of type IV glioblastoma multiform. Gliosarcomas are a mixture of glial and endothelial cells and are resistant to any chemotherapy.

TABLE 4

| Cell lines | Type | Origin | Source | $IC_{50}$ ($\times 10^{-6}$ M) |
|---|---|---|---|---|
| 9L | Gliosarcoma | Rat | ATCC | 6.82 ± 2.90 |
| GHD | Astrocytoma | Human | ATCC | 6.29 ± 2.98 |
| U 373 | Astrocytoma | Human | ATCC | 3.83 ± 1.37 |
| GL26 | Glioblastoma | Human | ATCC | 8.93 ± 1.10 |
| C6 | Glioblastoma | Rat | ATCC | 4.28 ± 2.82 |
| DN | Oligodendroglioma | Human | ATCC | 3.26 ± 0.93 |
| GHA | Oligodendroglioma | Human | ATCC | 1.78 ± 0.84 |

Example 6

In Vivo Efficacy in a Glioma Model

The aim of this study was to test whether the compound of Formula I administered by i.p. route prevents or delays tumor growth in C6 glioblastoma cell-bearing mice, and to determine an effective dosage regimen.

Animals: A total of 60 six-week-old female mice (Swiss nude mice), ranging between 18 to 25 g in weight, were observed for 7 days before treatment. Animal experiments were performed according to ethical guidelines of animal experimentation (*Charte du comité d'éthique du CNRS, juillet* 2003) and, the English guidelines for the welfare of animals in experimental neoplasia (WORKMAN et al. (1998), United Kingdom Coordinating Committee on Cancer Research (UKCCCR) "Guidelines for the welfare of animals in experimental neoplasia" (Second Edition, July 1998; *British Journal of Cancer* 77:1-10). Animals were maintained in rooms under controlled conditions of temperature (23±2° C.), humidity (45±5%), photoperiodicity (12 hrs light/12 hrs dark) and air exchange. Animals were housed in polycarbonate cages (5/single cage) that were equipped to provide food and water. Animal bedding consisted of sterile wood shavings that were replaced every other day. Food was provided ad libitum, being placed in the metal lid on the top of the cage. Autoclaved tap water was provided ad libitum. Water bottles were equipped with rubber stoppers and sipper tubes. Water bottles were cleaned, sterilized and replaced once a week. Two different numbers engraved on two earrings identified the animals. Each cage was labelled with a specific code.

Tumor Cell Line: The C6 cell line was derived from a rat glial tumor induced by N-nitrosomethyurea (NMU) (Premont et al. [3H] norepinephrine binding by rat glial cells in culture. Lack of correlation between binding and adenylate cyclase activation *Biochim Biophys Acta*. (1975) 381(2): 368-76).

Cells were grown as adherent monolayers at 37° C. in a humidified atmosphere (5% $CO_2$, 95% air). The culture medium was DMEM supplemented with 2 mM L-glutamine glutamine and 10% fetal bovine serum. For experimental use, tumor cells were detached from the culture flask by a 10 minute treatment with trypsin-versene. The cells were counted in a hemocytometer and their viability assessed by 0.25% trypan blue exclusion.

Preparation of the Test Article: For the test article, the following procedure was followed for reconstitution (performed immediately preceding injection). The vehicle consisted of a mixture of benzyl alcohol (1.5%), ethanol (8.5%), propylene glycol (PG) (27%), Polyethylene glycol (PEG) 400 (27%), dimethylacetamide (6%) and water (30%). The vehicle solution was first vortexed in order to obtain a homogeneous liquid. 0.6 mL of the vortexed vehicle solution was added to each vial containing the test article (the compound of Formula I). Vials were mixed thoroughly by vortexing for 1 minute and inverted and shaken vigorously. Vials were mixed again prior to injection into each animal.

Animal Inoculation with tumor cells: Experiment started at day 0 ($D_0$). On $D_0$, mice received a superficial intramuscular injection of C6 tumor cells ($5\times10^5$ cells) in 0.1 mL of DMEM complete medium into the upper right posterior leg.

Treatment Regimen and Results

Figure 2:
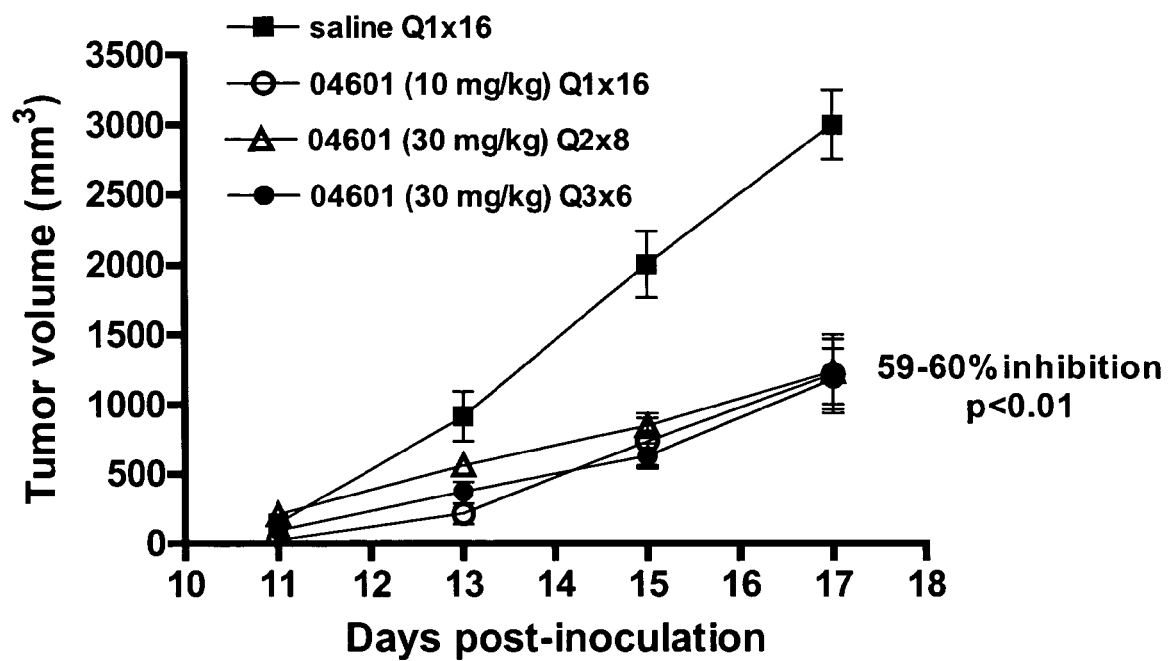
FIG. 2 shows inhibition of tumor growth resulting from administration of 10 to 30 mg/kg of the compound of Formula I to glioblastoma-bearing mice beginning one day after tumor cell inoculation.

In a first series of experiments, treatment started 24 hrs following inoculation of C6 cells. On the day of the treatment, each mouse was slowly injected with 100 μL of test or control articles by i.p. route. For all groups, treatment was performed until the tumor volume of the saline-treated mice (group 1) reached approximately 3 cm³ (around day 16). Mice of group 1 were treated daily with a saline isosmotic solution for 16 days. Mice of group 2 were treated daily with the vehicle solution for 16 days. Mice of group 3 were treated daily with 10 mg/kg of the compound of Formula I for 16 days. Mice of group 4 were treated every two days with 30 mg/kg of the compound of Formula I and received 8 treatments. Mice of group 5 were treated every three days with 30 mg/kg of the compound of Formula I and received 6 treatments. Measurement of tumor volume started as soon as tumors became palpable (>100 mm³; around day 11 post-inoculation) and was evaluated every second day until the end of the treatment using calipers. As shown in Table 5 and FIG. 2, the mean value of the tumor volume of all the compound of Formula I treated groups (6 mice/group) was significantly reduced as demonstrated by the one-way analysis of variance (Anova) test followed by the non-parametric Dunnett's multiple comparison test comparing treated groups to the saline group. An asterisk in the P value column of Table 5 indicates a statistically significant value, while "ns" signifies not significant.

TABLE 5

| Treatment | Treatment regimen | Tumor volume (mm³) (mean ± SEM) | % Inhibition | P value |
|---|---|---|---|---|
| Saline | Q1 × 16 | 3,004.1 ± 249.64 | — | — |
| Vehicle solution | Q1 × 16 | 2,162.0 ± 350.0 | 28.0% | >0.05 ns |
| Formula I (10 mg/kg) | Q1 × 16 | 1,220.4 ± 283.46 | 59.4% | <0.01* |
| Formula I (30 mg/kg) | Q2 × 8 | 1,236.9 ± 233.99 | 58.8% | <0.01* |
| Formula I (30 mg/kg) | Q3 × 6 | 1,184.1 ± 221.45 | 60.6% | <0.01* |

Figure 3:
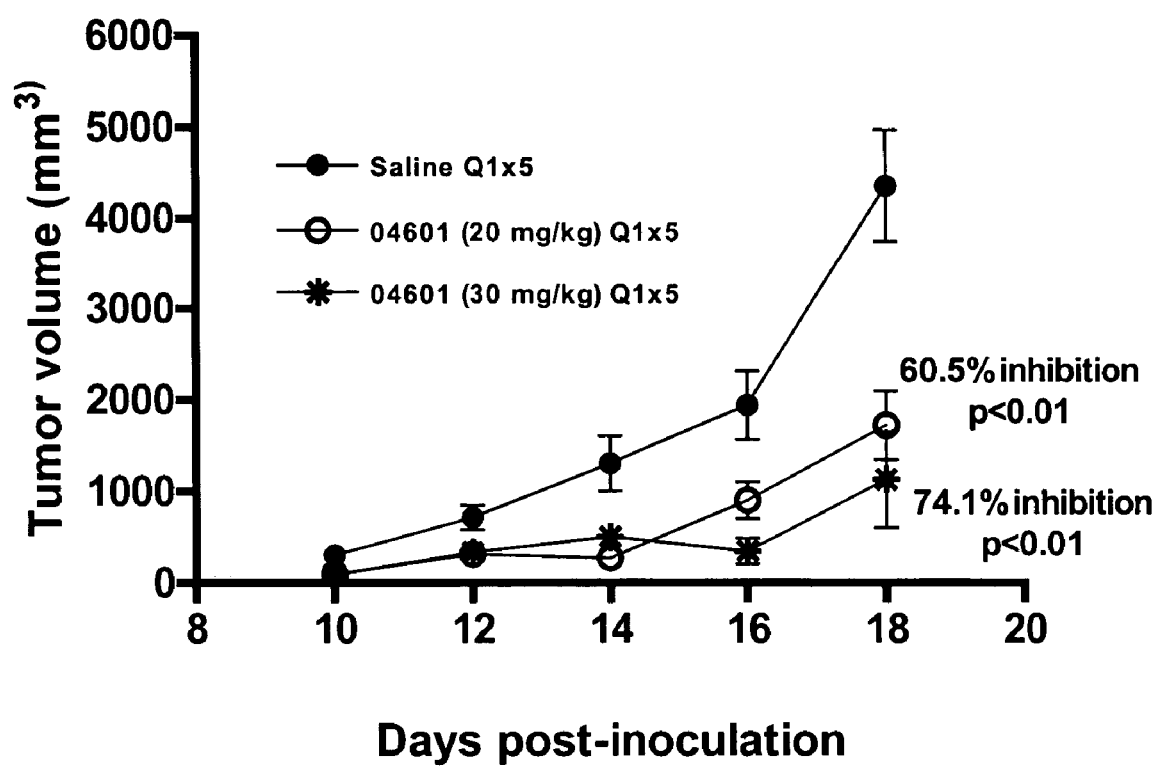
FIG. 3 shows inhibition of tumor growth resulting from administration of 20-30 mg/kg of the compound of Formula I to glioblastoma-bearing mice beginning ten days after tumor cell inoculation.

In a second series of experiments, treatment started at day 10 following inoculation of C6 cells when tumors became palpable (around 100 to 200 mm³). Treatment was repeated daily for 5 consecutive days. Mice of group 1 were treated daily with isotonic solution (0.9% saline). Mice of group 2 were treated daily with the vehicle solution. Mice of group 3 were treated daily with 20 mg/kg of the compound of Formula I. Mice of group 4 were treated daily with 30 mg/kg of the compound of Formula I. Compound of Formula I, saline, and vehicle solution were administered intraperitoneally in a volume of 100 microliters per 20 g body weight. Mice were treated until the tumor volume of the saline-treated control mice (group 1) reached approximately 4 cm³. Tumor volume was measured every second day until the end of the treatment using callipers. As shown in Table 6 and FIG. 3, the mean value of the tumor volume of all the compound of Formula I treated groups (6 mice/group) was significantly reduced as demonstrated by the one-way analysis of variance (Anova) test followed by the non-parametric Dunnett's multiple comparison test comparing treated groups to the saline group. An asterisk in the P value column of Table 6 indicates a statistically significant value, while "ns" signifies not statistically significant.

Histological analysis of tumor sections showed pronounced morphological changes between tumors treated with the compound of Formula I and control groups. In tumors treated with—treated tumors (20-30 mg/kg), cell density was decreased and the nuclei of remaining tumor cells appeared larger and pycnotic while no such changes were observed for vehicle-treated mice (FIG. 4).

TABLE 6

| Treatment | Treatment regimen | Tumor volume (mm³) (mean ± SEM) | % Inhibition | P value |
|---|---|---|---|---|
| Saline | Q1 × 5 | 4,363.1 ± 614.31 | — | — |
| Vehicle solution | Q1 × 5 | 3,205.0 ± 632.37 | 26.5% | >0.05 ns |
| Formula I (20 mg/kg) | Q1 × 5 | 1,721.5 ± 374.79 | 60.5% | <0.01* |
| Formula I (30 mg/kg) | Q1 × 5 | 1,131.6 ± 525.21 | 74.1% | <0.01* |

Example 7

Antitumor Efficacy of the Compound of Formula I Against Orthotopic C6 Glioma Tumor Xenograft The antitumor activity of the compound of Formula I was further tested in a orthotopic C6 glioma tumor xenograft model in mice. CD1 female nude mice (6 weeks of age) were grafted intra-cerebally with $5\times10^4$ (volume of 10 microliters) rat C6 glioma cells (day 0). Treatment was initiated 24 h after tumor cell implantation. The compound of Formula I was administered intraperitoneally (i.p.) at a concentration of 30 mg/kg (volume of 10 mL/Kg) on days 1, 2 and 3 followed by i.p. injections of 10 mg/kg on days 4 and 5 and 9 to 38. Vehicle (30% PEG; 30% PG; 40% H2O) was injected in a volume of 10 mL/Kg using the same route and schedule.

Figure 7:
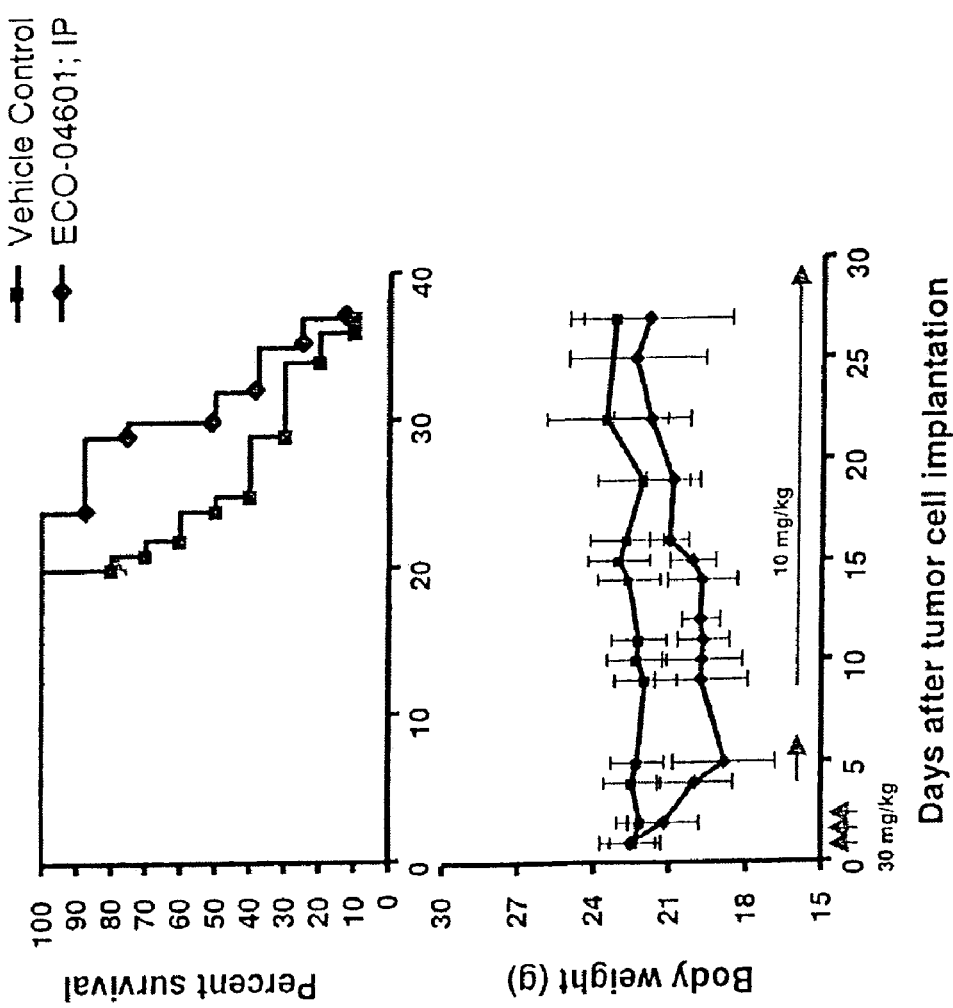
FIG. 7 shows the survival of mice xenografted with orthotopic C6 glioma tumor, treated daily with vehicle (squares) or the compound of Formula I (circles). Daily treatment with the compound of Formula I led to an increase survival of 7 days resulting in a 29% increase in life span.

Body weight of animals was monitored every other day and the effect of the compound of Formula I on growth of intracerebral glioma tumors was evaluated by mouse survival and percentage increase in life span (% ILS, expressed as mean survival time of treated animals minus the mean survival time of the control group). By criteria established by the National Cancer Institute, increases in life span exceeding 25% indicate that the drug has significant antitumor activity (Plowman et al. (1997) Human tumor xenografts models in NCI drug development. In: Theicher BA (ed) Anticancer drug development guide: prescreening, clinical trials and approval. Human press, Totowa, pp 101-125). Statistical analysis of mouse survival was performed by Kaplan-Mayer analysis. Daily treatment with the compound of Formula I led to an increase survival of 7 days resulting in a 29% increase in life span (see FIG. 7).

Example 8

Pharmacokinetics

The compound of Formula I was dissolved in ethanol (5%), Polysorbate 80 (15%), PEG 400 (5%) and dextrose (5%) at a final concentration of 6 mg/ml (iv, ip and sc administration). For oral administration, the compound of Formula I was solubilized in Chremopor® EL/Ethanol (50%:50%) at a final concentration of 6 mg/ml. Prior to dosing, animals (female Crl: CD1 mice; 6 weeks of age, 22-24 g) were weighed, randomly selected and assigned to the different treatment groups. ECO-4601 was administered by the intravenous (iv), subcutaneous (sc), intraperitoneal (ip), or oral (po) route to the assigned animals. The dosing volume of ECO-4601 was 5 mL per kg body weight. Animals were anesthetized prior to bleeding with 5% isoflurane. Blood was collected into microtainer tubes containing the anticoagulant $K_2EDTA$ by cardiac puncture from each of 4 animals per bleeding timepoint (2 min, 5 min, 15 min, 30 min, 1 h, 2 h, 4 h and 8 h). Following collection, the samples were centrifuged and the plasma obtained from each sample was recovered and stored frozen (at approximately $-80°$ C.) pending analysis. At the 5 min and 30 min time points, the following organs were harvested from each animal: brain, lungs, skeletal muscle, fat tissue, kidneys, spleen, thymus and liver. Tissues were frozen (at approximately $-80°$ C.) pending analysis.

Samples were analysed by LC/MS/MS. Standard curve ranged from 25 to 2000 ng/mL with limit of quantitation (LOQ)$\leq$25 ng/mL and limit of detection (LOD) of 10 ng/mL.

Plasma values of the compound of Formula I falling below the limit of quantitation (LOQ) were set to zero. Mean concentration values and standard deviation (SD) were calculated at each timepoints of the pharmacokinetic study (n=4 animals/timepoint). The following pharmacokinetic parameters were calculated: area under the plasma concentration versus time curve from time zero to the last measurable concentration time point (AUC0-t), area under the plasma concentration versus time curve extrapolated to infinity (AUCinf), maximum observed plasma concentration (Cmax), time of maximum plasma concentration (tmax), apparent first-order terminal elimination rate constant (kel), apparent first-order terminal elimination half-life will be calculated as 0.693/kel ($t_{1/2}$). The systemic clearance (CL) of the compound of Formula I after intravenous administration was calculated using Dose/AUCinf. Pharmacokinetic parameters were calculated using Kinetica™ 4.1.1 (InnaPhase Corporation, Philadelphia, Pa.).

Results

Figure 5:
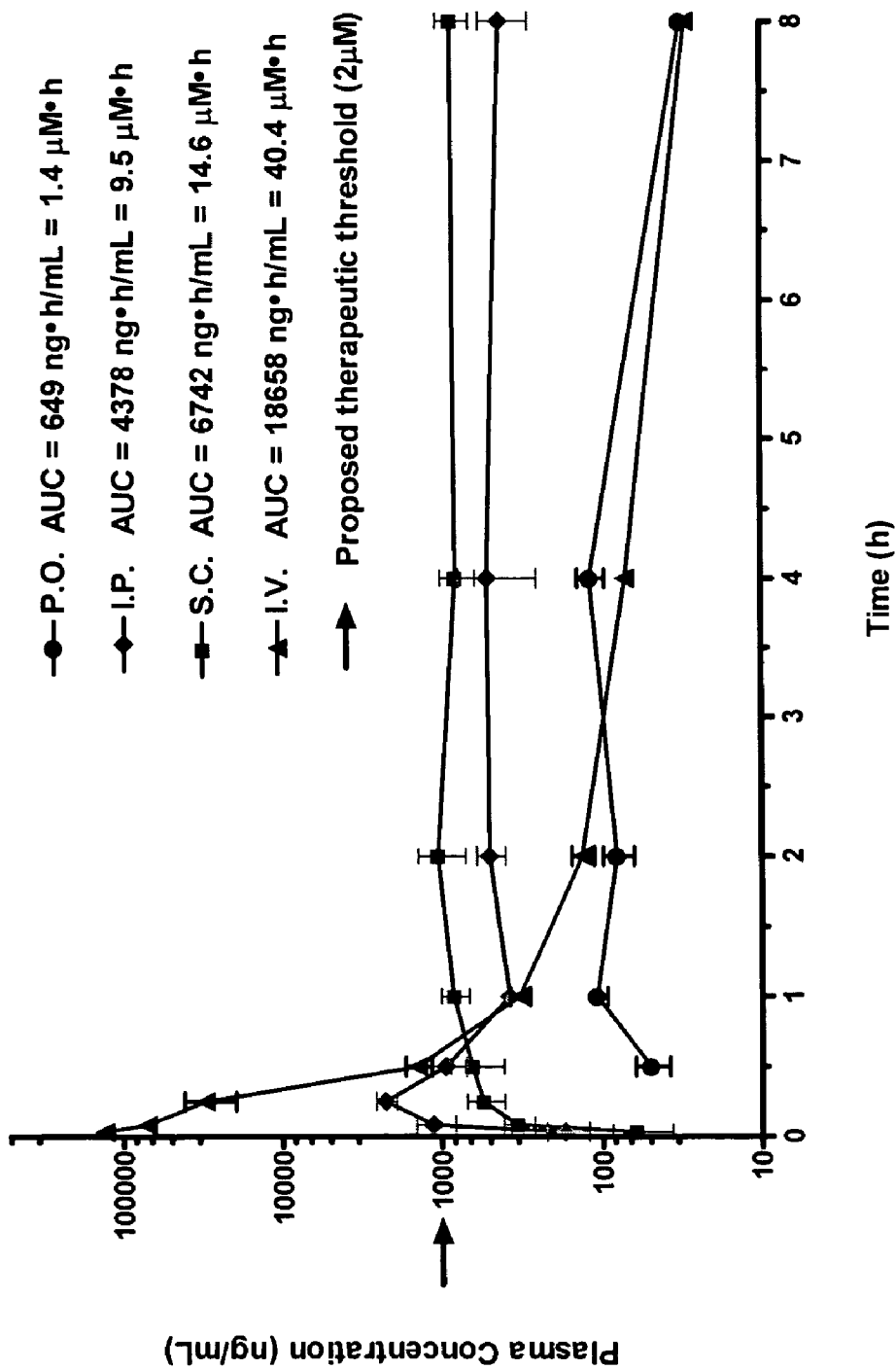
FIG. 5 shows the mean (±SD) plasma concentrations of the compound of Formula I in Swiss mice following 30 mg/kg intravenous (iv), intraperitoneal (ip), subcutaneous (sc) and oral (po) administrations.

Mean plasma concentrations of the compound of Formula I following intravenous (iv), intraperitoneal (ip), subcutaneous (sc), and oral (po) administrations at 30 mg/kg are presented in FIG. 5.

Mean ($\pm$SD) plasma concentrations of the compound of Formula I following I.V. administration of a 30 mg/kg dose declined rapidly in a biexponential manner resulting in very short half lives ($t_{1/2}$ $\alpha$ and $\beta$ of 4.6 min and 2.56 h, respectively). On the other hand, the pharmacokinetics of the compound of Formula I following intraperitoneal and subcutaneous administrations showed a PK profile suggestive of slow release. With both these routes of administration, the compound plasma concentration is sustained and maintained at therapeutically relevant levels for over 8 hours. Oral administration results in moderate but sustained drug levels. These data indicate that the compound of Formula I is orally bioavailable (~5-8% when compared to IV bolus administration).

Figure 6:
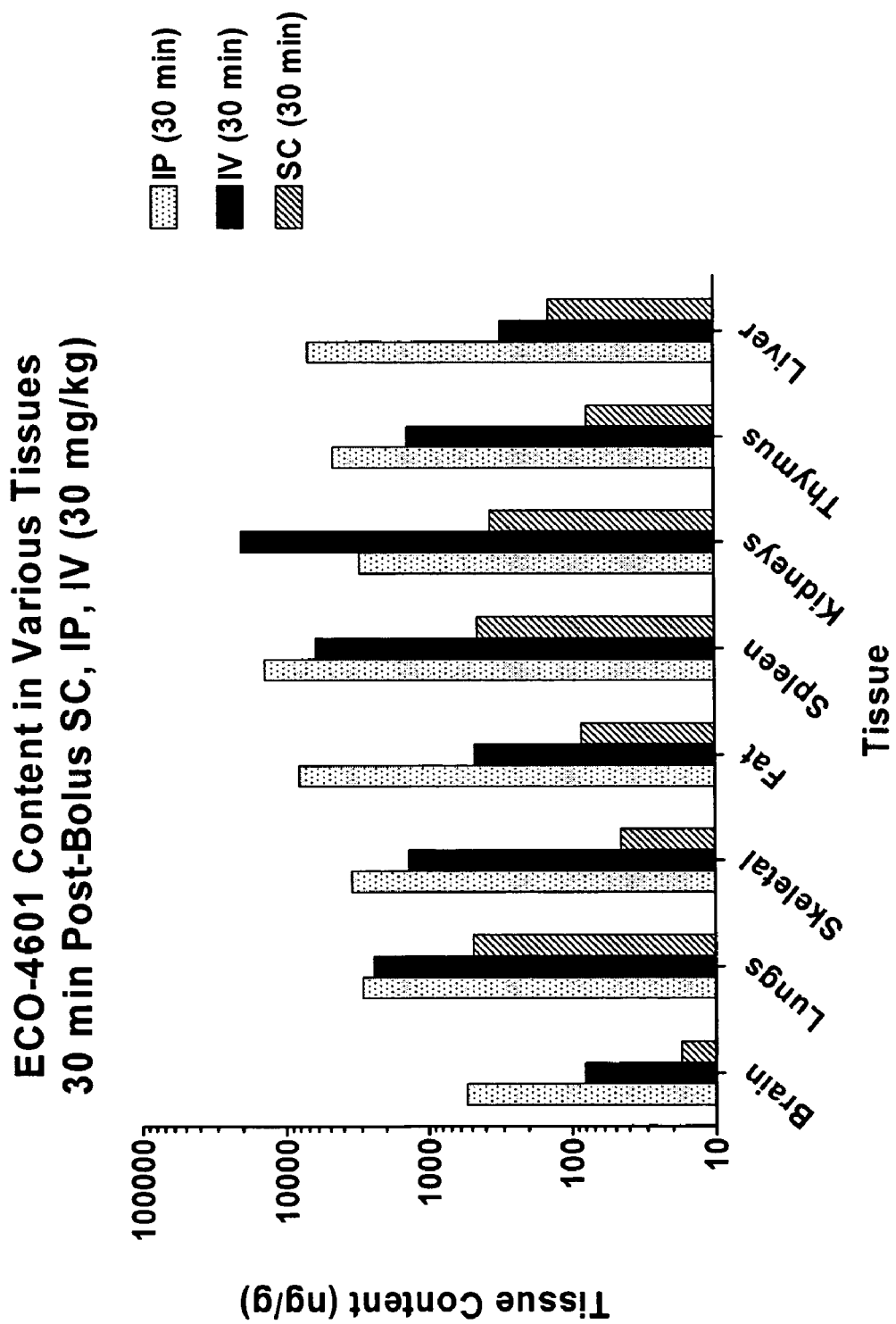
FIG. 6 shows the mean concentration of the compound of Formula I in various tissues, 30 minutes after 30 mg/kg intravenous (iv), intraperitoneal (ip) and subcutaneous (scadministrations.

Mean tissue concentrations of the compound of Formula I 30 min after intravenous (iv), intraperitoneal (ip) or subcutaneous (sc) administrations at 30 mg/kg are presented in FIG. 6. The 30 min time point was chosen since plasma concentrations were similar with all three routes of administration. Compound of Formula I is well distributed following iv and ip dosing. Surprisingly, although ip and sc administrations resulted in a similar PK profile, tissue levels were significantly lower following sc dosing. This could be explained by the absence of peak levels following sc administration compared with iv and ip administrations.

Example 9

Anticancer Efficacy of the Compound of Formula I Against Murine P388 Leukemia Model The anticancer activity of the compound of Formula I was further tested in a murine P388 leukemia model in mice.

Formulation: The drug ECO-4601 is first dissolved in 1 volume of 90% propylene glycol (PG). This is followed by the addition of 2 volumes of 45% polyethylene glycol 400 (PEG 400). The volume ratio of PEG 400/PG/water is respectively 30:30:40. Compound is injected in a volume of 10 mL/kg.

DBA/2 female mice (6 weeks of age) were injected intraperitoneally (ip) with $1\times10^6$ P388 murine leukemia cells (day 0). Mice were randomized in 4 groups (10 mice per group) at Day 1 and treated with the following dose and schedule.

Group1: iv injection of vehicle (PEG/PG formulation) on D1 and D8, daily ip administration of vehicle from D2 to D7 and from D9 to D10

Group 2: iv injection of ECO-4601 in PEG-PG formulation at 50 mg/kg on D1 followed by daily ip administration of ECO-4601 in PEG-PG formulation at 10 mg/kg from D2 to D4 and from D6 to D12

Group 3: Daily ip administration of ECO-4601 in PEG-PG formulation at 10 mg/kg from D1 to D4 and from D8 to D14

Mice body weights were recorded twice a week. Lethality and behaviour of animals were recorded every day. All vehicle control mice died between D8 to D10 from peritoneal carcinomatosis associated with ascites. Three (3) mice from group 2 died one day after treatment due to compound toxicity. The remaining seven (7) died between days 8 and 12. Mice from group 3 died between days 8 and 12. The results are expressed as percent of mean survival time of treated animals over the mean survival time of the control group (treated vs control, T/C %) and as increase life span (mean survival time of treated animals minus that of control animals over the mean survival time of the control group; ILS %). By NCI criteria, T/C exceeding 125% and ILS increasing 25% indicate that the drug has significant anticancer activity.

Compared with vehicle-treated mice, % T/C were 133.3% and 138.9% and ILS 33 and 38.9 for groups 2 and 3, respectively. These results indicate a moderate but significant enhancement of survival time of P388 IP leukemia bearing mice treated with ECO-4601.

TABLE 7

Effect of ECO-4601 on survival of DBA/2 mice bearing IP murine leukemia

| Groups | Treatment | Mean Survival Days ± SD | Median survival | % T/C | % ILS |
|---|---|---|---|---|---|
| 1 | PEG-PG Vehicle IV (days 1 and 8) | 9 ± 0.8 | 9 | | |

TABLE 7-continued

Effect of ECO-4601 on survival of DBA/2 mice bearing IP murine leukemia

| Groups | Treatment | Mean Survival Days ± SD | Median survival | % T/C | % ILS |
|---|---|---|---|---|---|
| 2 | IP (days 2-7 and 9-10) ECO-4601 IV 50 mg/kg (day 1) IP 10 mg/kg (days 2-4 and 6-12) | 11 ± 1.5 | 12 | 133.3 | 33 |
| 3 | ECO-4601 IP 10 mg/kg (days 1-4 and 8-14) | 12.6 ± 4.9 | 12.5 | 138.9 | 38.9 |

Example 10

Antitumor Efficacy of the Compound of Formula I Against Human PC3 Prostate Cancer Model The anticancer activity of the compound of Formula I was further tested in a human PC3 prostate model in mice. HRLN male nude mice (8 weeks of age) were implanted with 1 mm$^3$ PC3 tumor fragments subcutaneously (sc) in the right flank. Animals were randomized (ten per group) when tumors reach an average size of 80-120 mg and treatment began according to the table below. For these studies, ECO-4601 was formulated in 5% ethanol, 5% PEG-400 and 15% Polysorbate -80 in dextrose 5%.

TABLE 8

| Gr. | N | Agent | Dose (mg/kg) | Conc. of solution mg/mL | Route & Dosing volume (mL/kg) | Schedule |
|---|---|---|---|---|---|---|
| 1 | 10 | Cyclophosphamide | 90 | 9 | ip/10 | qd x5 |
| 2 | 10 | D5W | — | — | sc/5 | 5/2/5/2/5 |
| 3 | 10 | ECO-4601 | 30 | 6 | sc/5 | 5/2/5/2/5 |
| 4 | 10 | ECO-4601 | 50 | 10 | sc/5 | q3d x7 |
| 5 | 10 | ECO-4601 | 30 | 6 | ip/5 | q3d x7 |
| 6 | 10 | ECO-4601 | 100 | 10 | iv/10 | 5/2/5/2/5 |

Tumor measurements were taken twice weekly using callipers and were converted to tumor mass (in milligrams) using the formula: with$^2$ (mm)×length (mm)×0.52. Body weights were also recorded twice weekly. Statistical analysis was done using the unpaired two-tailed Student's t test.

% T/C was calculated at day 38 once animals in the control group had to be sacrificed due to antitumor burden. Intravenous treatment did not result in activity (likely due to short half-life and lack of sustaining therapeutically effective drug levels). On the other hand, subcutaneous administration at 30 mg/kg given from days 1 to 5, 8 to 12 and 15 to 19, or at 50 mg/kg every three days×7 (days 1, 4, 7, 10, 13, 16 and 19) where we maintain drug levels at therapeutically effective drug concentrations for over 8 hours resulted in significant antitumor activity with % T/C of 25.5% and 14.6%, respectively (P<0.0001).

Figure 8:
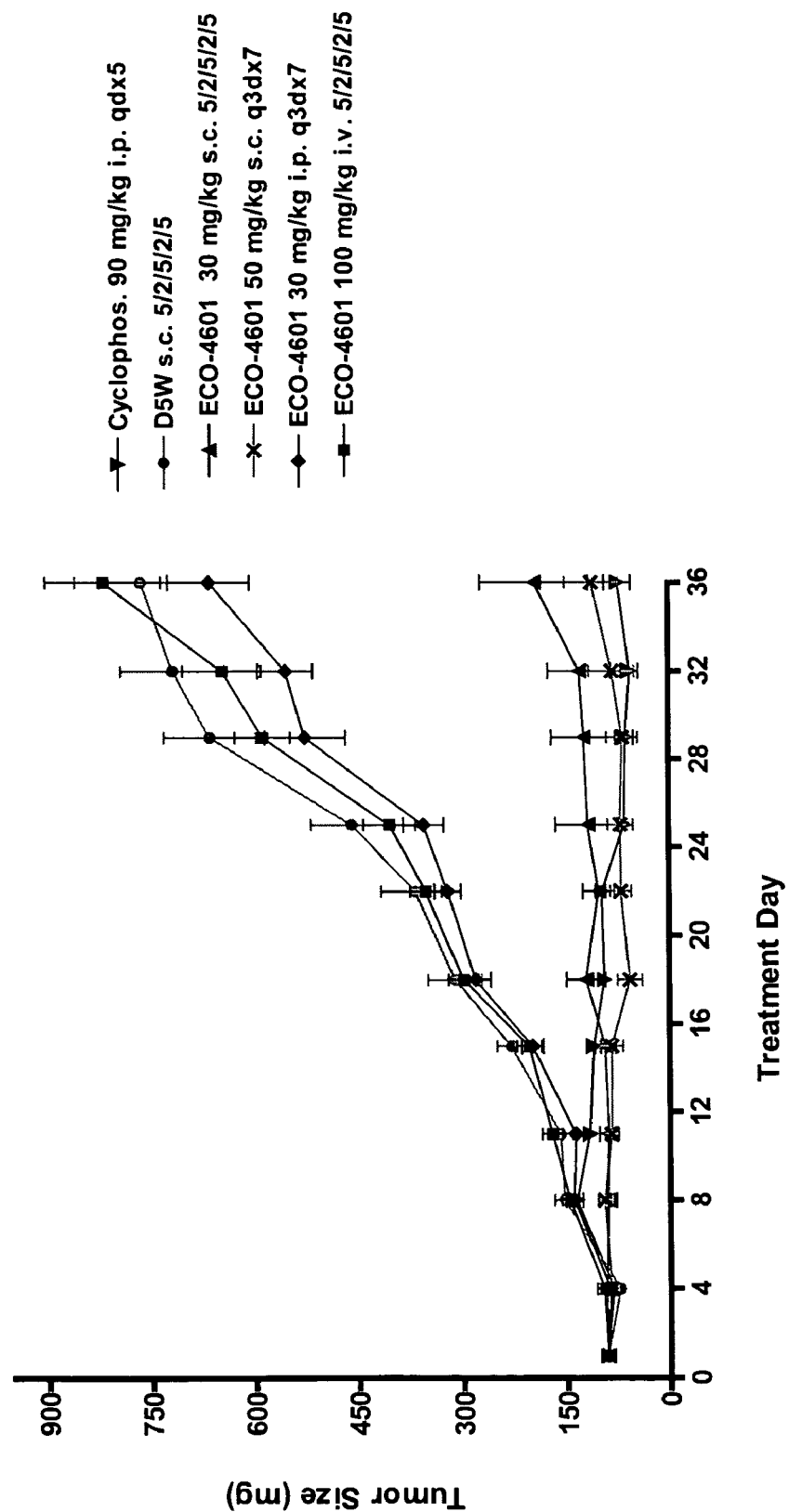
FIG. 8 shows the antitumor efficacy of the compound of Formula I against human prostate tumor (PC3) xenografts in male Harlan nude mice.
Figure 9:
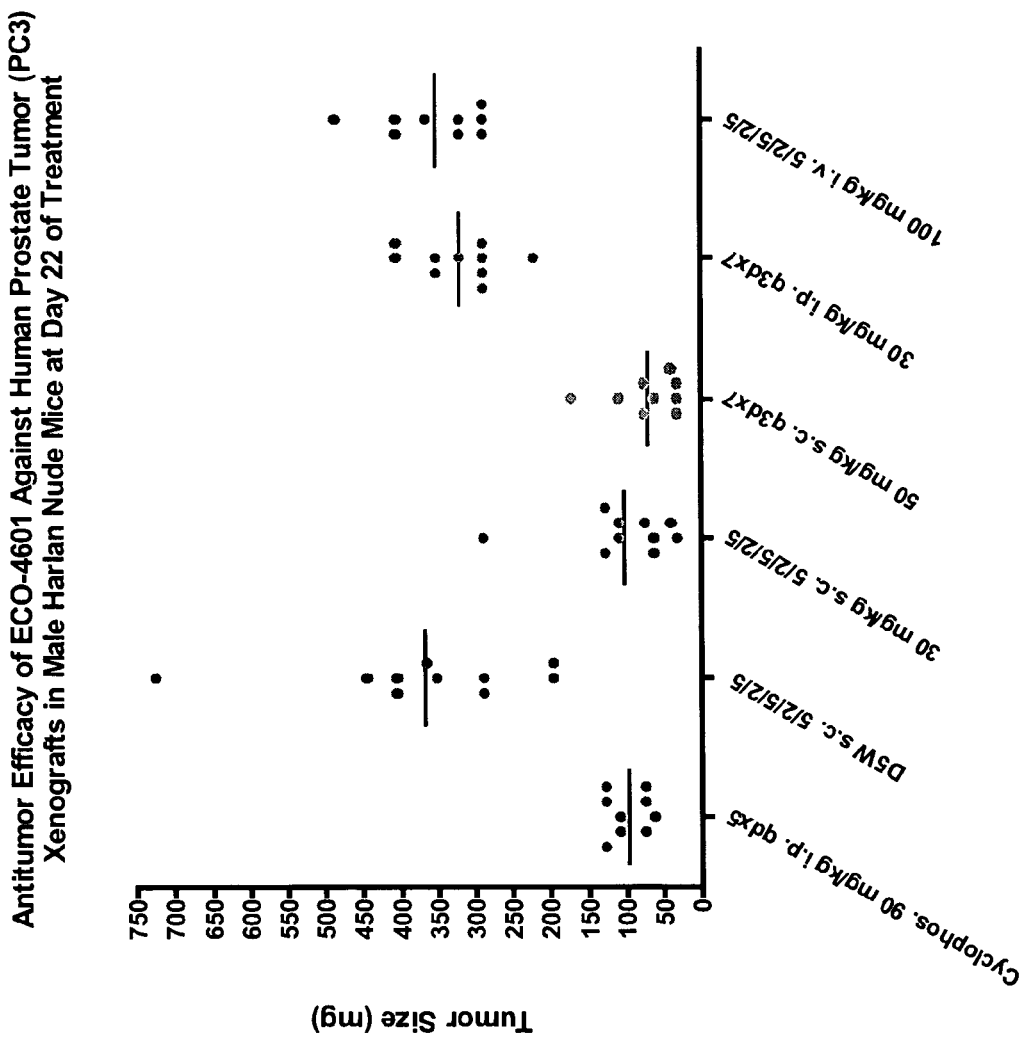
FIG. 9 shows the antitumor efficacy of the compound of Formula I against human prostate tumor (PC3) xenografts on individual male Harlan nude mice at day 22 of treatment.

FIG. 8 shows antitumor efficacy results of the compound of Formula I against an prostate tumor xenografts. FIG. 9 shows antitumor efficacy results on idual animals on the 22$^{nd}$ day of treatment.

Example 11

Antitumor Efficacy of the Compound of Formula I Against Human MDA-MB-231 Breast Cancer Model The antitumor activity of the compound of Formula I was further tested in a human MD-MB-231 breast cancer model in mice. HRLN female nude mice (8 weeks of age) were treated with 5×10$^6$ MDA-MB-231 tumor cells (sc) in the right flank. Animals were randomized (ten per group) when tumors reach an average size of 80-120 mg and treatment began according to the table below. For these studies, ECO-4601 was formulated in 5% ethanol, 5% PEG-400 and 15% Polysorbate 80 in dextrose 5% (formulation B).

TABLE 9

| Gr | N | Agent | Dose (mg/kg) | Conc. of solution mg/mL | Volume of injection (mL/kg) | Route | Schedule |
|---|---|---|---|---|---|---|---|
| 1 | 10 | D5W | — | | 10 | iv | 5/2/5/2/5 |
| 2 | 10 | paclitaxel | 30 | | | iv | qod x5 |
| 3 | 10 | Vehicle | — | | 5 | sc | qd x21 |
| 4 | 10 | ECO-4601 | 100 | 10 | 10 | iv | 5/2/5/2/5 |
| 5 | 10 | ECO-4601 | 30 | 6 | 5 | sc | 5/2/5/2/5 |
| 6 | 10 | ECO-4601 | 20 | 6 | 3.3 | sc | qd x21 |
| 7 | 10 | ECO-4601 | 50 | 10 | 5 | sc | q3d x7 |
| 8 | 10 | ECO-4601 | 30 | 6 | 5 | ip | q3d x7 |

Tumor measurements were taken twice weekly using calipers and were converted to tumor mass (in milligrams) using the formula: with$^2$ (mm)×length (mm)×0.52. Body weights were also recorded twice weekly. Statistical analysis was done using the unpaired two-tailed Student's t test.

% T/C was calculated at day 21 once animals in the control group had to be sacrificed due to tumor burden. Intravenous treatment did not result in activity (likely due to short half-life and lack of sustaining therapeutically effective drug levels). On the other hand, subcutaneous administration at 20 mg/kg given everyday for 21 days or at 30 mg/kg given from days 1 to 5, 8 to 12 resulted in significant antitumor activity with % T/Cs of 40% and 35% respectively; P<0.0001). Subcutaneous or intraperitoneal administration at 50 and 30 mg/kg respectively every three days×7 (days 1, 4, 7, 10, 13, 16 and 19) were also effective giving moderate but statistically significant T/C values of 68% (P=0.0019) and 58% (P=0.0007).

Figure 10:
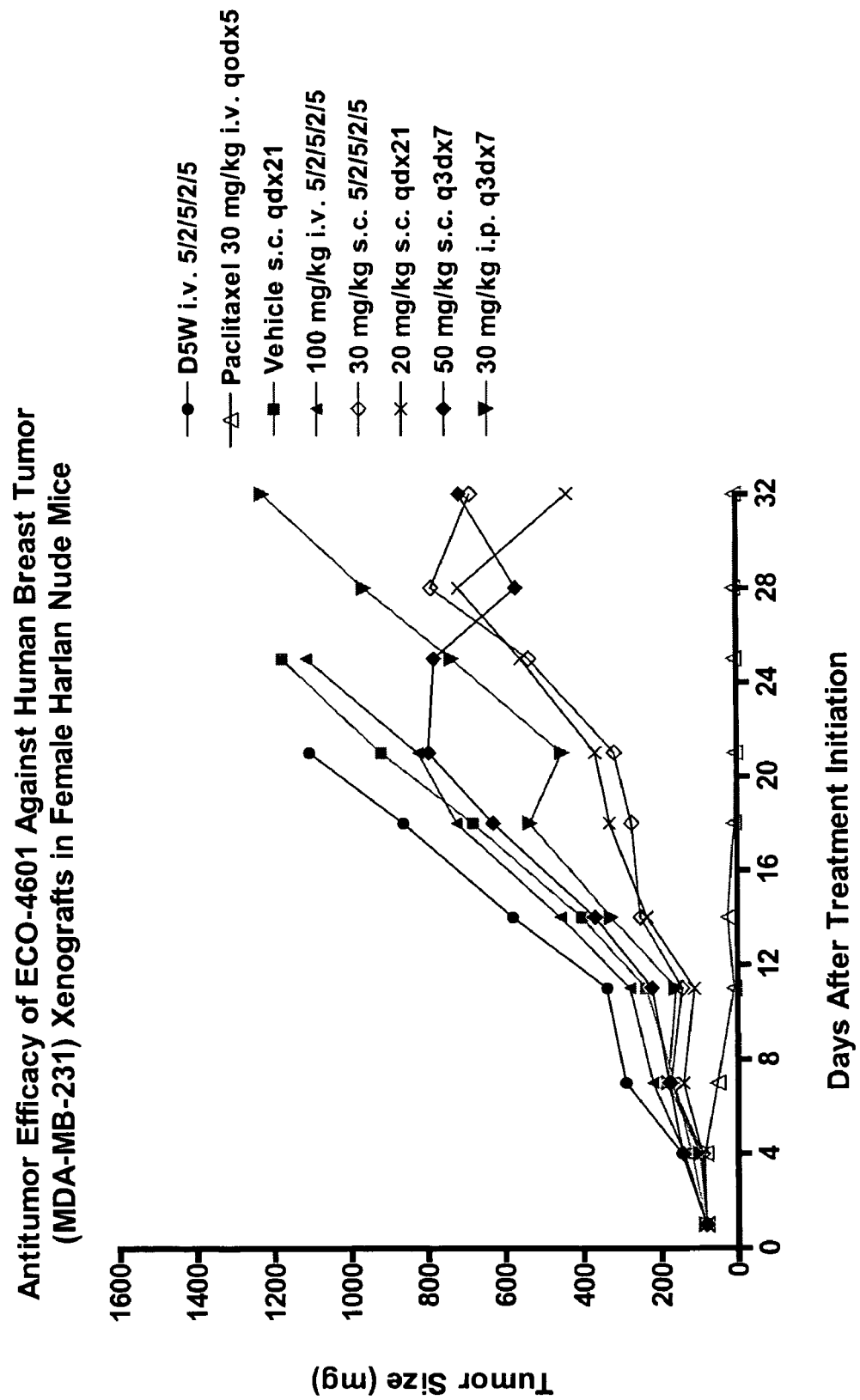
FIG. 10 shows the antitumor efficacy of the compound of Formula I against human breast tumor (MDA-MB-231) xenografts in female Harlan nude mice.
Figure 11:
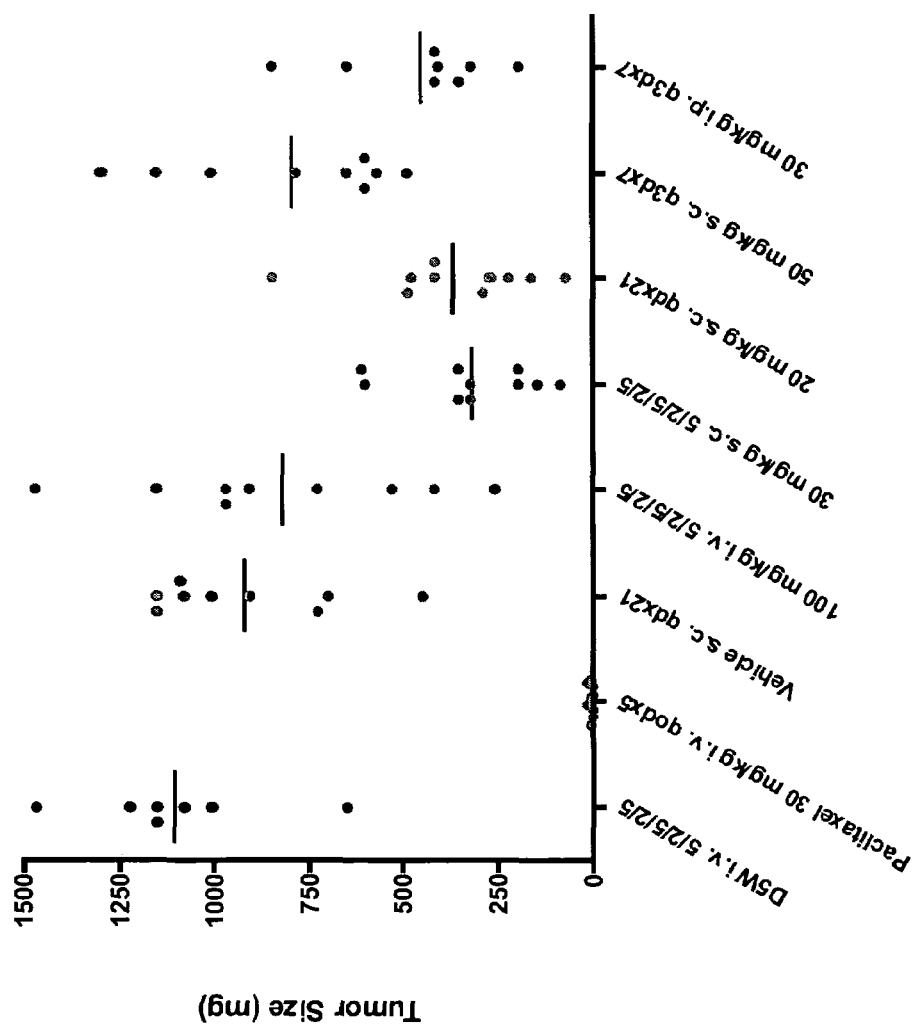
FIG. 11 shows the antitumor efficacy of the compound of Formula I against human breast tumor (MDA-MB-231) xenografts on individual female Harlan nude mice at day 21 of treatment.

FIG. 10 shows antitumor efficacy results of the compound of Formula I against human breast tumor xenografts. FIG. 11 shows antitumor efficacy results on the 21$^{st}$ day of treatment.

Example 12

PBR Binding Affinity

The compound of Formula I was tested for peripheral benzodiazepine receptor (also referred to as PBR) binding affinity. This receptor is known to be involved in anticancer activity of known compounds. Data were also compared to inhibition of GABA$_A$ Central Benzodiazepine Receptor (CBR), to show selectivity. Binding results for both receptors were obtained by radioligand binding as a quantitation method.

The general procedure used to determine PBR percentage binding is described in Le Fur et al (1983), *Life Sci. USA*, vol 33, 449-457, which is incorporated by reference in its entirety. The conditions used are as follows: Source of PBR:

Wistar rat heart; Ligand: 0.3 nM [$^3$H]PK-11195; Incubation: 15 minutes in incubation buffer (50 mM Tris-HCl, pH 7.5, 10 mM MgCl$_2$) at 25° C.; and nonspecific ligand: Dipyridamole (100 µM, K$_D$: 2.3 nM, B$_{max}$: 0.17 pmol/mg protein, Specific binding: 90%).

The general procedure used to determine CBR percentage binding is described in Damm et al (1978), *Res. Comm. Chem. Pathol. Pharmacol.*, vol 22, 597-600 and Speth et al (1979), *Life Sci.*, vol 24, 351-357), which are incorporated herein by reference in their entirety. The conditions used are as follows: Source of CBR: Wistar rat brain; Ligand: 1 nM [$^3$H]flunitrazepam; Incubation: 60 minutes in incubation buffer (50 mM Na-K phosphate, pH 7.4) at 25° C.; and nonspecific ligand: Diazepam (Non specific ligand: 10 µM, K$_D$: 4.4 nM, B$_{max}$: 1.2 pmol/mg protein, Specific binding: 91%).

Binding Assays were done at constant concentration of the compound, in 1% DMSO as vehicle. The results are expressed as percentage inhibition. Significance was obtained when a result was $\geq$50% binding or inhibition.

Results: 80% binding activity to the peripheral benzodiazepine receptor was obtained at a constant concentration of 1 µM of the compound of Formula I, while only a 39% binding activity to the central benzodiazepine receptor was obtained at a constant concentration of 10 µM.

PBR binding studies using multiple dilutions indicated that the compound of Formula I had an inhibition concentration (IC50) value of 0.291 µM and an inhibition constant (Ki) of 0.257 µM, compared to the binding results above, which showed an IC50 above 10 µM in the inhibition of CBR.

Also treatment of animals with the compound of Formula I resulted in an increased expression of several genes involved in steroid biosynthesis, cholesterol transport/metabolism, signal transduction and apoptosis, which is consistent with the compound of Formula I acting as a PBR ligand.

Example 13

In Vivo Administration of Farnesyl Dibenzodiazepinone

In this example, a pharmaceutical composition comprising a therapeutically effective amount of a farnesyl dibenzodiazepinone compound of the invention, in combination with a pharmaceutically acceptable carrier or excipient, is administered to a patient for treatment of cancer. Examples of suitable carriers are found in standard pharmaceutical texts, e.g. "Remington's Pharmaceutical Sciences," 16th edition, Mack Publishing Company, Easton, Pa., 1980.

Formulation and Dosage

The dosage of the farnesyl dibenzodiazepinone compound will vary depending on the form of administration. In the case of an intravenous injection, the therapeutically effective dose of farnesyl dibenzodiazepinone per injection is in a dosage range of approximately 0.1-750 milligram/kg body weight per day, for example at a dose of 10 milligrams/kg of body weight per day. Dosage in human in mg/m$^2$ is determined from the dosage obtained in animal models, for example, the dosage in mg/kg in mice would be multiplied by about 3 Frereich E. J. et al., Cancer Chemother. Rep. (1966); 50(4):219-244 to obtain the approximate dosage in mg/m$^2$ required for humans The starting dose for initiating clinical trials in humans with a cytotoxic drug in oncology is one-tenth of the dose lethal to 10% or rodents on a body surface area basis (DeGeore et als., Regulatory considerations for preclinical development of anticancer drugs, 1998, Cancer Chemother. Pharmacol., 41: 173-185). In addition to the active ingredient, the compositions usually also contain suitable buffers, for example phosphate buffer, to maintain an appropriate pH and sodium chloride, glucose or mannitol to make the solution isotonic. The administering physician will determine the daily dosage that will be most suitable for an individual and will vary with the age, gender, weight and response of the particular individual, as well as the severity of the patient's symptoms. The above dosages are exemplary of the average case. There can, of course, be individual instances where higher or lower dosage ranges are merited, and such are within the scope of this invention. The farnesyl dibenzodiazepinone compounds of the present invention may be administered alone or in combination with other pharmaceuticals.

Toxicity and Therapeutic Efficacy

Toxicity and therapeutic efficacy of farnesyl dibenzodiazepinone compounds can be determined by standard pharmaceutical procedures in cell cultures or experimental animals. Therapeutic efficacy is determined in animal models as described above and in the examples herein. Toxicity studies are done to determine the lethal dose for 10% of tested animals (LD10). Animals are treated at the maximum tolerated dose (MTD): the highest dose not producing mortality or a greater than 20% body weight loss. The effective dose (ED) is related to the MTD in a given tumor model to determine the therapeutic index (MTD/ED) of the compound.

The data obtained from cell culture assays and animal studies can be used in formulating a range of dosage for use in humans. The dosage of compositions of the invention will generally be within a range of circulating concentrations that include the ED$_{50}$ with little or reversible toxicity. The dosage may vary within this range depending upon the dosage form employed and the route of administration utilized. For any compound used in the method of the invention, the therapeutically effective dose can be estimated initially from cell culture assays. A dose may be formulated in animal models to achieve a circulating plasma concentration range of the compound. Such information can be used to more accurately determine useful doses in humans. Levels in plasma may be measured, for example, by high performance liquid chromatography.

Example 14

Intravenous Delivery of Farnesyl Dibenzodiazepinone—Toxicity Study

In this example, pharmaceutical compositions comprising farnesyl dibenzodiazepinone are delivered via intravenous infusion to Cynomolgus monkeys for evaluation of toxicity and toxicokinetic profile. A trial dose is administered by bolus intravenous injection (Preliminary Phase), and the results of this treatment are used to select a starting dose for the Main Phase. Young adult Cynomolgus monkeys (*Macaca Fasicularis*) weighing between 2 and 5.5 kg may be purchased from Covance Research Products Inc, P.O. Box 549, Alice, Tex., 78333, USA.

Preliminary Phase

Compositions comprising farnesyl dibenzodiazepinone are administered to a single Cynomolgus monkey on two occasions, by bolus intravenous injection. Following the first dose, the monkey is observed for clinical signs of reaction to treatment. A second dose level is then selected based upon the observations following the first dose. Subsequent to the second dose, which is administered at least 24 hours following the first administration, the monkey is observed for clinical signs of reaction to treatment, and blood is collected for toxicokinetic analysis.

Main Phase

The Main Phase consists of four groups of animals, each group comprising one male and one female. As described below, a solution of farnesyl dibenzodiazepinone is administered at one of three different dose levels to the animals of each of three groups of cynomolgus monkeys. Dose levels for the Main Phase of the study are selected based partially upon the results of the Preliminary Phase. The relevant dose is delivered to each appropriate animal of Groups 2, 3, and 4 by continuous (24 hours/day) intravenous infusion, via a surgically implanted vascular catheter, for 7 days. The animals of Group 1 are treated under similar conditions with a solution of the vehicle control. Prior to initiation of treatment, as well as at termination, blood and urine samples are collected for clinical pathology. Upon completion of the treatment period, all surviving animals are subjected to a necropsy examination.

TABLE 10

| Group Numbers | Group Designation | Dose Level (mg/kg/day) | Dose Concentration (mg/mL) | Number of animals | |
|---|---|---|---|---|---|
| | | | | Male | Female |
| 1 | Vehicle Control | 0 | 0 | 1 | 1 |
| 2 | Low Dose | TBD | TBD | 1 | 1 |
| 3 | Mid Dose | TBD | TBD | 1 | 1 |
| 4 | High Dose | TBD | TBD | 1 | 1 |

Dose Levels

Dose levels may be selected based on available data from infusion studies conducted in smaller animals, such as rodents (e.g., rats), and following a single bolus IV dose. In female rats, for example, the bolus IV MTD may be 70 mg/kg while a 7d CIV may be 110 mg/kg/day. These doses (converted to the equivalent mg/sq.m. dose in the monkey) are used to determine starting doses.

| Formulation: | |
|---|---|
| Active agent: | Farnesyl dibenzodiazepinone |
| Control/Carrier: | 0.9% Saline, Polyethylene Glycol 400, ethanol, and Polysorbate 80 |

Administration of the Test and Control Compositions

During the Preliminary Phase, the test composition (active agent plus carrier) is administered once daily (5 mL/kg) by intravenous injection for two consecutive days, the second dose having been selected based upon observations following the first dose. The test and control compositions are infused intravenously (24 hours/day) for 7 consecutive days during the Main Phase.

Toxicity and Toxicokinetics

During the Preliminary Phase, a series of 3 blood samples (approximately 1 mL each) are collected from the monkey on Day 2 of the treatment period, at 5 minutes, 30 minutes, and 2 hours after treatment. Blood samples (approximately 1 mL each) are collected from each monkey at one time point daily for 7 days (at approximately the same time each day) during the Main Phase. Samples intended for plasma extraction are centrifuged (approximately 4° C.) and the resulting plasma is recovered and stored frozen (approximately −20/−80° C.) in labeled vials or tubes. Blood and urine samples are collected and analyzed using any of a variety of well-known clinical pathological techniques, including, without limitation, hematology, coagulation, clinical chemistry, urinalysis, and histological evaluation.

What is claimed is:

1. A method for inhibiting growth or proliferation of a neoplastic cell, comprising contacting a neoplastic cell with a compound of formula I:

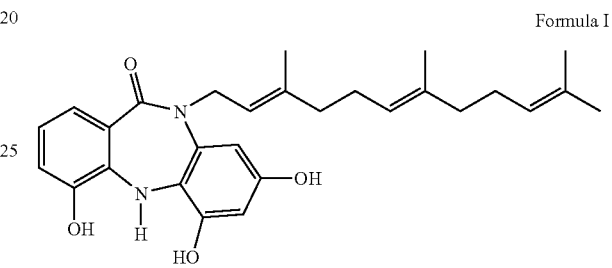

Formula I thereby inhibiting growth or proliferation of a neoplastic cell, wherein the neoplastic cell is a neoplastic cell of a neoplastic disorder is selected from the group consisting of a solid neoplasm, hematopoietic disorder, pancreatic cancer, prostate cancer, colorectal cancer, lung cancer, a neuroblastoma, ovarian cancer, melanoma, breast cancer, renal cancer and liver cancer.

2. The method of claim 1 wherein the neoplastic cell is a neoplastic cell of a solid neoplasm.

3. The method of claim 1 wherein the neoplastic cell is a neoplastic cell of a hematopoietic disorder.

4. A method for treating a neoplastic disorder in a mammal, comprising administering a compound of formula I:

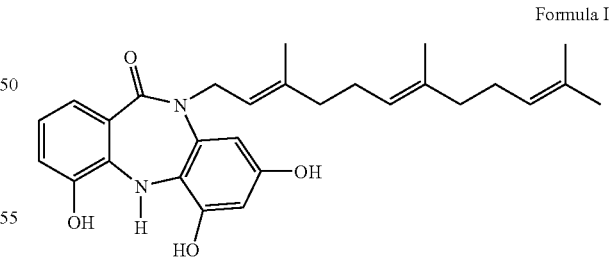

Formula I or a pharmaceutically acceptable salt thereof to a mammal in need of treatment, thereby treating a neoplastic disorder in a mammal, wherein the neoplastic disorder is selected from the group consisting of a hematopoietic disorder, pancreatic cancer, prostate cancer, colorectal cancer, lung cancer, a neuroblastoma, ovarian cancer, melanoma, breast cancer, renal cancer and liver cancer.

5. The method of claim 4 wherein the hematopoietic disorder is leukemia or lymphoma.

6. A method of treating prostate cancer in a mammal, comprising administering a compound of formula I:

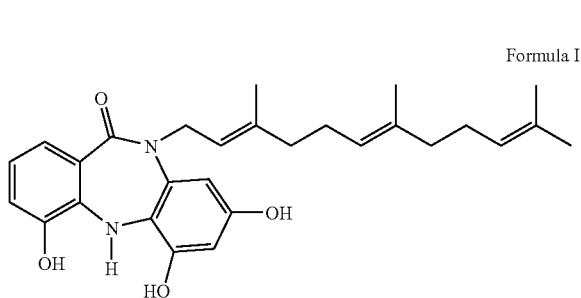

Formula I or a pharmaceutically acceptable salt thereof to a mammal in need of treatment, thereby treating prostate cancer in a mammal.

7. A method of treating breast cancer in a mammal, comprising administering a compound of formula I:

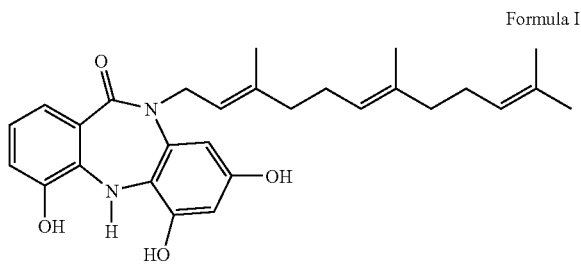

Formula I or a pharmaceutically acceptable salt thereof to a mammal in need of treatment, thereby treating breast cancer in a mammal.

8. A method of treating brain cancer in a mammal, comprising administering a compound of formula I:

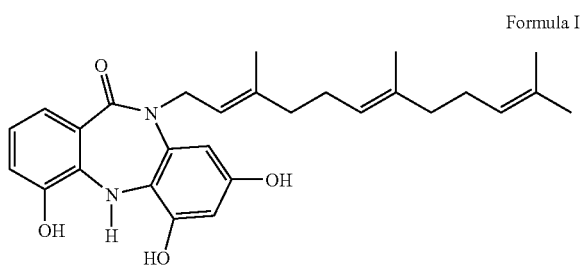

Formula I or a pharmaceutically acceptable salt thereof to a mammal in need of treatment, thereby treating brain cancer in a mammal.

9. A method of treating leukemia in a mammal, comprising administering a compound of formula I:

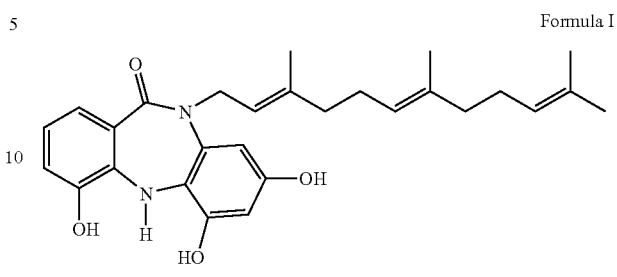

Formula I or a pharmaceutically acceptable salt thereof to a mammal in need of treatment, thereby treating leukemia in a mammal.

10. The method of any one of claims 4 and 5 to 9, wherein the mammal is a human.

11. The method of any one of claims 4, 6, 7, 8 and 9 wherein the compound of formula I is formulated to be administered by intravenous infusion.

12. The method of any one of claims 4, 6, 7, 8 and 9 wherein the compound of formula I is formulated to be administered by injection.

13. A method for inhibiting the growth or proliferation of a neoplastic cell in a mammal, comprising administering a pharmaceutical composition comprising a compound of formula I:

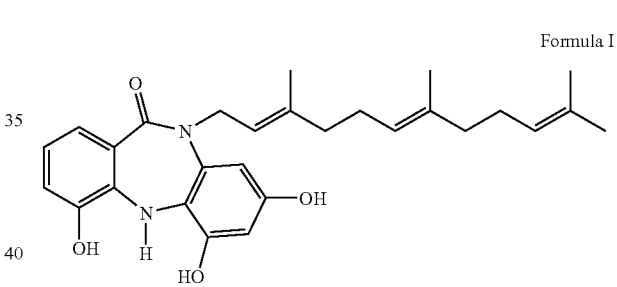

Formula I or a pharmaceutically acceptable salt thereof, together with a pharmaceutically acceptable carrier, to a mammal in need of such inhibiting, thereby inhibiting the growth or proliferation of a neoplastic cell in a mammal, wherein the neoplastic cell is a cell of a neoplastic disorder selected from the group consisting of a hematopoietic disorder, pancreatic cancer, prostate cancer, colorectal cancer, lung cancer, a neuroblastoma, ovarian cancer, melanoma, breast cancer, renal cancer and liver cancer.

14. A method for treating a neoplasm in a mammal, comprising administering a pharmaceutical composition comprising a compound of formula I:

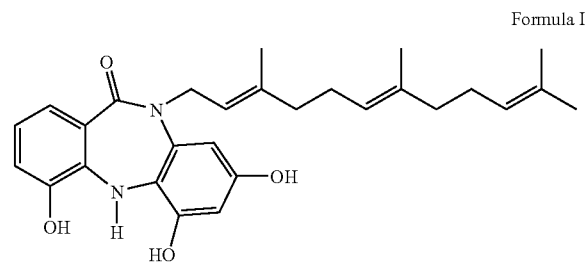

Formula I or a pharmaceutically acceptable salt thereof, together with a pharmaceutically acceptable carrier, to a mammal in need of treatment, thereby treating a neoplasm in a mammal, wherein the neoplasm is selected from the group consisting of a hematopoietic neoplasm, pancreatic cancer, prostate cancer, colorectal cancer, lung cancer, a neuroblastoma, ovarian cancer, melanoma, breast cancer, renal cancer and liver cancer.

15. The method of claim 13 or 14, wherein the compound of formula I is formulated for administration by a means selected from the group consisting of oral, parenteral, sublingual, intranasal, intraocular, rectal, transdermal, mucosal and topical administration.

16. The method of claim 13 or 14, wherein the compound of formula I is formulated for administration by intravenous infusion.

17. The method of claim 13 or 14, wherein the compound of formula I is administered in a dosage unit in the range of 0.01 to 750 milligrams (mg) per kilogram body weight of the mammal.

18. The method of claim 13 or 14, wherein the mammal is a human.

19. The method of claim 13 or 14, wherein the compound of formula I is administered in a dosage unit in the range of 0.37 to 111 milligrams per square meter (mg/m$^2$).

20. The method of claim 13 or 14, wherein the pharmaceutical composition is administered in a single dose.

21. A method of treating pancreatic cancer in a mammal, comprising administering a compound of formula I:

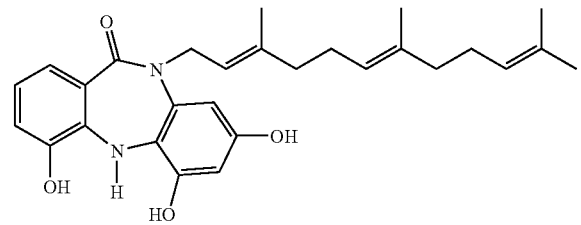

Formula I or a pharmaceutically acceptable salt thereof to a mammal in need of treatment, thereby treating pancreatic cancer in a mammal.

* * * * *